United States Patent
Sun

(10) Patent No.: US 11,331,417 B2
(45) Date of Patent: May 17, 2022

(54) MAGNETIC TARGET SEPARATION INSTRUMENT AND APPLICATION THEREOF

(71) Applicant: SHANGHAI CLINICAL ENGINE TECHNOLOGY DEVELOPMENT CO., LTD., Shanghai (CN)

(72) Inventor: Yinghao Sun, Shanghai (CN)

(*) Notice: Subject to any disclaimer, the term of this patent is extended or adjusted under 35 U.S.C. 154(b) by 536 days.

(21) Appl. No.: 15/763,639

(22) PCT Filed: Sep. 26, 2016

(86) PCT No.: PCT/CN2016/100776
§ 371 (c)(1),
(2) Date: Mar. 27, 2018

(87) PCT Pub. No.: WO2017/054749
PCT Pub. Date: Apr. 6, 2017

(65) Prior Publication Data
US 2018/0280039 A1 Oct. 4, 2018

(30) Foreign Application Priority Data
Sep. 29, 2015 (CN) .......................... 201510631394.5

(51) Int. Cl.
*A61L 31/02* (2006.01)
*A61B 17/22* (2006.01)
(Continued)

(52) U.S. Cl.
CPC ........ *A61L 31/028* (2013.01); *A61B 1/00165* (2013.01); *A61B 1/00195* (2013.01);
(Continued)

(58) Field of Classification Search
CPC . A61B 1/00165; A61B 1/00195; A61B 1/051; A61B 17/00; A61B 17/22;
(Continued)

(56) References Cited

U.S. PATENT DOCUMENTS 4,240,410 A 12/1980 Pickering et al.
4,279,245 A * 7/1981 Takagi .................. F16L 11/125
600/139
(Continued)

FOREIGN PATENT DOCUMENTS

CN 87206141 U 1/1988
CN 1328065 A 12/2001
(Continued)

OTHER PUBLICATIONS

Office Action (both in Russina and English translations) from corresponding Russian Application 2018115691 dated May 7, 2019.
(Continued)

*Primary Examiner* — Jocelin C Tanner
(74) *Attorney, Agent, or Firm* — Abelman, Frayne & Schwab; Stefan Knirr

(57) ABSTRACT

The present invention relates to nanoparticles, a preparation method thereof, a stone removal device, a magnetic target separation instrument and its application. The nanoparticles include a nanoparticle core made of magnetic materials, and a nanoparticle shell formed by attaching surface modifier monomers to the nanoparticle core with an initiator and/or a crosslinking agent. The prepared nanoparticles can wrap stones in ureter, and then small stones remaining in body can be removed quickly without damage from the body under the action of the magnetic target separation instrument. The stones can be drawn and moved without injuring ureteral wall, and meanwhile be disposed conveniently without easy shift.

14 Claims, 19 Drawing Sheets

(51) Int. Cl.
| | |
|---|---|
| *A61B 34/00* | (2016.01) |
| *A61L 31/04* | (2006.01) |
| *A61B 1/00* | (2006.01) |
| *A61B 1/05* | (2006.01) |
| *A61B 17/225* | (2006.01) |
| *A61L 31/14* | (2006.01) |
| *A61L 31/10* | (2006.01) |
| *B82Y 5/00* | (2011.01) |
| *A61B 17/00* | (2006.01) |

(52) U.S. Cl.
CPC ............. *A61B 1/051* (2013.01); *A61B 17/22* (2013.01); *A61B 17/225* (2013.01); *A61B 34/73* (2016.02); *A61L 31/02* (2013.01); *A61L 31/022* (2013.01); *A61L 31/04* (2013.01); *A61L 31/048* (2013.01); *A61L 31/10* (2013.01); *A61L 31/14* (2013.01); *B82Y 5/00* (2013.01); *A61B 2017/00477* (2013.01); *A61B 2017/00526* (2013.01); *A61B 2017/00734* (2013.01); *A61B 2017/00876* (2013.01); *A61B 2017/22082* (2013.01); *A61B 2017/22087* (2013.01); *A61L 2400/12* (2013.01)

(58) Field of Classification Search
CPC ... A61B 17/225; A61B 17/52; A61B 17/2251; A61B 34/73; A61B 2017/00345; A61B 2017/00477; A61B 2017/00526; A61B 2017/00734; A61B 2017/00876; A61B 2017/22082; A61B 2017/22087; A61L 31/02; A61L 31/022; A61L 31/028; A61L 31/04; A61L 31/048; A61L 31/10; A61L 31/14; B22F 1/0044; B22F 1/0062; A61N 2/004

See application file for complete search history.

(56) References Cited

U.S. PATENT DOCUMENTS

| | | | | |
|---|---|---|---|---|
| 4,802,461 | A * | 2/1989 | Cho | A61B 1/0051 600/108 |
| 5,228,453 | A * | 7/1993 | Sepetka | A61M 25/09 600/434 |
| 5,357,961 | A * | 10/1994 | Fields | A61M 25/0102 600/435 |
| 5,364,404 | A | 11/1994 | Jaffe et al. | |
| 5,682,894 | A * | 11/1997 | Orr | A61M 25/09 600/431 |
| 6,157,853 | A * | 12/2000 | Blume | A61B 34/73 600/426 |
| 6,817,364 | B2 * | 11/2004 | Garibaldi | A61M 25/0127 128/899 |
| 6,875,220 | B2 | 4/2005 | Du et al. | |
| 7,066,924 | B1 * | 6/2006 | Garibaldi | A61M 25/0127 604/164.13 |
| 8,328,820 | B2 * | 12/2012 | Diamant | A61B 17/22012 606/128 |
| 8,690,907 | B1 * | 4/2014 | Janardhan | A61B 17/12109 606/200 |
| 9,925,311 | B2 | 3/2018 | Grunwald et al. | |
| 2004/0243119 | A1 * | 12/2004 | Lane | A61B 18/02 606/21 |
| 2005/0033162 | A1 * | 2/2005 | Garibaldi | A61B 1/00158 600/429 |
| 2005/0033314 | A1 * | 2/2005 | Sakurai | A61B 17/2202 606/127 |
| 2008/0140101 | A1 * | 6/2008 | Carley | A61B 17/320758 606/159 |
| 2008/0270948 | A1 * | 10/2008 | Lazzaro | G06F 3/0482 715/854 |
| 2009/0136594 | A1 * | 5/2009 | McLeroy | A61B 17/221 424/648 |
| 2009/0138594 | A1 | 5/2009 | McLeroy et al. | |
| 2009/0187077 | A1 * | 7/2009 | Hosoda | A61B 1/00034 600/178 |
| 2011/0028785 | A1 * | 2/2011 | Chen | A61B 1/00183 600/109 |
| 2012/0130164 | A1 | 5/2012 | Palese | |
| 2013/0197297 | A1 * | 8/2013 | Tekulve | A61N 2/002 600/12 |
| 2014/0357806 | A1 | 12/2014 | Song et al. | |
| 2015/0164803 | A1 | 6/2015 | Hakata et al. | |
| 2015/0217003 | A1 | 8/2015 | Garcia-Esteller et al. | |
| 2016/0074561 | A1 | 3/2016 | Grunwald et al. | |
| 2018/0280039 | A1 | 10/2018 | Sun | |

FOREIGN PATENT DOCUMENTS

| | | |
|---|---|---|
| CN | 101173025 A | 5/2008 |
| CN | 201108459 Y | 9/2008 |
| CN | 202020520 U | 11/2011 |
| CN | 202020521 U | 11/2011 |
| CN | 202096278 U | 1/2012 |
| CN | 202096279 U | 1/2012 |
| CN | 10242494 A | 8/2013 |
| CN | 203208098 U | 9/2013 |
| EP | 1371690 A2 | 12/2003 |
| EP | 2502882 A1 | 9/2012 |
| EP | 2796101 A1 | 4/2013 |
| EP | 2796101 A1 | 10/2014 |
| GB | 2406276 A | 3/2005 |
| JP | H0538342 A | 2/1993 |
| JP | 2004043802 A | 2/2004 |
| JP | 2004135782 A | 5/2004 |
| JP | 2005120365 A | 5/2005 |
| JP | 2009116186 A | 5/2009 |
| JP | 2018-535226 A | 1/2010 |
| JP | 2015511938 A | 4/2015 |
| JP | 2015528283 A | 9/2015 |
| JP | 2016522811 A | 8/2016 |
| KR | 20150104901 A | 9/2015 |
| RU | 2334477 C2 | 9/2008 |
| RU | 2516961 C1 | 5/2014 |
| WO | 2009133418 A1 | 5/2009 |
| WO | 2009070766 A2 | 6/2009 |
| WO | 2011062217 A1 | 5/2011 |
| WO | 2014028537 | 2/2014 |
| WO | 2014173468 A1 | 10/2014 |
| WO | 2014194102 | 12/2014 |
| WO | 2014194102 A1 | 12/2014 |

OTHER PUBLICATIONS

Search Report (both in Russian and English translations) from corresponding Russian Application 2018115691 dated May 7, 2019.
Office Action and Search Report from RU 2018111957 dated Feb. 20,k 2019 (Russian and English translations of both Office Action and Search Report are provided).
Y. K. Tan, et al., "In Vitro Comparison of Prototype Magnetic Tool with Conventional Nitinol Basket for Ureteroscopic Retrieval of Stone Fragments Rendered Paramagnetic with Iron Oxide Microparticles," J. Urol., 188(2):648-652 (2012).
R. Fernandez, et. al., "Determining a Performance Envelope for Capture of Kidney Stones Functionalized with Superparamagnetic Microparticles," J. Endurology, 26(9):1227-1230 (2012).
Office Action from RU Application No. 2018114445 dated Feb. 13, 2019 (English translation included).
Search Report from RU Application No. 2018114445 dated Feb. 12, 2019.
Extended European Search Report for EP 16 85 0377 dated Feb. 25, 2019.
Office Action from CN 201510631394.5 dated Dec. 21, 2018.
International Search Report from corresponding PCT Application No. PCT/CN2016/100776 dated Dec. 27, 2016.
Supplementary European Search Report dated May 19, 2019 for EP 16850373.

(56) References Cited

OTHER PUBLICATIONS

Y. K. Tan, et al., "In Vitro Comparison of Prototype Magnetic Tool with Conventional Nitinol Basket for Ureteroscopic Retrieval of Stone Fragments Rendered Paramagnetic with Iron Oxide Microparticles," J. Urol., 188(2):648-552 (2012).

Bio-Nobile: "PickPen 1-M Magnetic Device—Instructions for use," Bio-Nobile Oy, pp. 1-4 (May 1, 2003).

Office Action from corresponding JP Application, JP 2018-836226 dated Apr. 18, 2019.

Chad R. Tracy, et al., "Rendering Stone Fragments Paramagnetic With Iron-oxide Microparticles Improves the Efficiency and Effectiveness of Endoscopic Stone Fragment Retrieval," Urology, 76:5:1266e10-14 (2010).

Jianping GE, et al., "One-Step Synthesis of Highly Water-Soluble Magnetic Colloidal Nanocrystals," Chem. Eur. J., 13:7153-7161 (2007).

Fangjie Xu et al., "Magnetite Nanocrystal Clusters with Ultra-High Sensitivity in Magnetic Resonance Imaging," ChemPhysChem, 13:336-341 (2012).

Office Action from corresponding Japanese Patent Application No. 2018-535225 dated Mar. 30, 2020 (Original and English translation).

Office Action from corresponding Korean Patent Application No. 10-2018-7012108 dated Apr. 10, 2020 (Original and English translation).

Vestal, et al., "Atom Transfer Radical Polymerization Syntheses and Magnetic Characterization of MnFe2O4 / Polystyrene Core Shell Particles" JACS 124:14312-14313 (2002).

Notice of Non-Final Rejection from Korean Patent Application No. 10-2018-7012062 dated Jan. 30, 2020 (Korean and English translation).

\* cited by examiner

MAGNETIC TARGET SEPARATION INSTRUMENT AND APPLICATION THEREOF

TECHNICAL FIELD

The present invention relates to nanoparticles, a method for preparing the same, a stone removal device comprising nanoparticles, a magnetic target separation instrument and its application.

BACKGROUND ART

Urinary calculi/stone (urolithiasis) have an incidence as high as 5%-10%, and can be found in any part of kidney, bladder, ureter and urethra, in which stones in kidney and ureter are common. It is found in clinical observation that calcium-containing stones are the most common types of urinary stones, that is, about 70% to 80% of all urinary stones. At present, there are only a few cases of calcium-containing stones which pathological causes have been clearly revealed, while the causes for most of calcium-containing stones are not yet clear. According to chemical composition, stones can be divided into four categories: calcium-containing stones, infection induced stones, uric acid stones and cystine stones. Calcium-containing stones can be divided into following types: simple calcium oxalate, calcium oxalate with calcium phosphate, calcium oxalate with a small amount of uric acid; the main components of infection induced stones are ammonium magnesium phosphate and hydroxyapatite; uric acid stones can be divided into following types: uric acid, uric acid amine, or those containing a small amount of calcium oxalate in addition to the above ingredients; cystine stones can be divided into following types: simple cystine, or cystine with a small amount of calcium oxalate.

Soft/hard ureteroscopic lithotripsy is performed through natural channel of the human body, has the advantages of small trauma and definite lithothriptic effect, and is currently the main treatment means for most of ureteral stones and kidney stones. However, the current soft/hard ureteroscopic lithotripsy also has some deficiencies: 1) upper ureteral stones and fragments of stones in ureter may be easily brought back to kidney by the infused water or the recoil force of lithotripsy tools; 2) there is lack of a fast, safe and effective method to take out residual debris of stones in ureteral lumen and kidney calices. It is an important mean to prevent ureteral stones from being recoiled back to kidney that a tool is used to block the ureter above the ureteral stones. At present, there are also some ureteral occluders in clinical practice, and such kind of stones blocking tools are also commonly used to remove stones. However, these ureteral occluders still have some shortcomings in actual use. Stone baskets (such as various stone baskets described in Patent Publication No. JP2009536081A, DE19904569A1, WO2004056275A1, WO2011123274A1 are designed with a net bag) are the most commonly used stone interception and removal tools, which cross over stone and then are opened to form a net so as to prevent the upward drift of stone debris, and at the same time, the stone baskets are also used as stone removal tools to net and take out small stone debris. However, the amount of stone removed by the stone basket every time is limited, so that multiple feeds of ureteroscope are needed, while repeated injection of water and feeds of ureteroscope would increase the risk of residual debris drift; secondly, the use of basket to take stones has great randomness, that is, it is a kind of contingency that the stones enter the basket and fall out of the basket, the basket would not be withdrawn from the ureter if too much stones enter the basket, and the efficiency would be very low if too less stones enter the basket so that more time is required for shaking, thereby extending the operation time, increasing the risk of surgery or anesthesia as well as the cost; thirdly, some stones in special parts such as stones in lower kidney calices can hardly be accessed by endoscopy itself, and the bending performance of endoscopy would decline when a stone basket is introduced, so it occurs frequently that the stones can be seen but cannot be taken out, and it is often needed to press abdomen or adjust posture to assist the removal of stones, which render the operation difficult and inefficient. In addition, the stone basket cannot completely seal the ureteral lumen, and there is still a chance that stones escape from the basket, and smaller stone debris are difficult to remove through the stone basket and generally have to be excreted naturally, which usually result in an extended time for removing stones or incomplete removal of stones, while these residual debris would further play the role of "crystal nucleus" to cause recurrence of stones easily. Moreover, the edges of stones in stone basket may be easily squeezed out from basket holes, and thus may easily scratch the ureter wall when the stones are dragged and removed, thereby causing complications in severe cases. In summary, there is an urgent need for a material and method for removal of stones in urinary system that can collect stones, facilitate the stone taking, do not damage the ureteral wall when the stones are dragged, can be conveniently disposed and are not easy to cause shift of stone.

Contents of the Invention

The present invention is aimed to solve the problem of residual stone debris and difficult removal thereof in the conventional soft/hard ureteroscopic lithotripsy. Therefore, a first object of the present invention is to provide a nano-material that can be used safely and efficiently to remove a stone located at a position such as kidney, ureter and so on in an urinary system; a second object of the present invention is to provide a method for preparing the nano-material with different morphological structures; a third object of the present invention is to provide a use of the nano-material in coordination with a selfmade magnetic target separation instrument in an operation of urinary calculi; a fourth object of the present invention is to provide a use of the nano-material in manufacture of an article for removing a stone in urinary system.

According to the first aspect of the present invention, there is provided a nanoparticle comprising a nanoparticle core composed of a magnetic material; and a nanoparticle shell formed by attaching a surface modifier monomer to the nanoparticle core with an initiator and/or a crosslinking agent.

According to some embodiments of the present invention, the nanoparticle wraps a stone through physical adsorption, chemical bonding, and photosensitive, thermosensitive, and pH-sensitive crosslinking. Specifically, the binding and wrapping forces between the nanoparticles and the stone include: van der Waal's force, hydrophobic interaction, adsorption and surface deposition for binding and wrapping; covalent bonds formed between carboxyl-stone, including hydrogen bonds, ester bonds, amide bonds, and other covalent bonds; physical entanglement and chemical crosslinking between chains.

According to some embodiments of the present invention, the nanoparticle core has a diameter of 2-50 nm, and a weight percentage of 30-95% relative to the whole weight of the nanoparticle, and the magnetic material constituting the core comprises a compound of $Fe^{3+}$, $Fe^{2+}$, $Mn^{2+}$ or $Ni^{2+}$, or a metal element selected from iron, nickel, copper, cobalt, platinum, gold, europium, gadolinium, dysprosium, terbium, or a composite or oxide of the aforementioned metals, or a combination of two or more of the above items, preferably one of or a combination of any two of $Fe^{3+}$, $Fe^{2+}$, $Mn^{2+}$ or $Ni^{2+}$, more preferably $Fe^{3+}$ and $Fe^{2+}$ in a ratio of 15% to 85%, preferably 1:2.5 to 1.5:1. It should be noted that the method for preparing the nanoparticle used in the present invention can well control the size and dimension of the magnetic nanoparticle core; especially, in comparison with the nanoparticles prepared by other methods, among the parameters of the nanoparticle obtained in the present invention that relates to the biomedical application, the dispersibility of the nanoparticle is very good and less than 1.1.

According to certain embodiments of the present invention, the surface modifier includes a surface modifier with hydrophilic, hydrophobic, photosensitive, thermosensitive or pH sensitive function response, wherein the hydrophilic surface modifier includes acrylic acid, methacrylic acid, isobutyl acrylamide or poly N-substituted isopropylacrylamide; the hydrophobic surface modifier comprises oletins, preferably polystyrene, polyethylene or oleic acid; the photosensitive surface modifier is selected from the group consisting of azos and quinolines and benzophenones (PVBP), preferably vinyl benzophenone; the thermosensitive surface modifier is selected from the group consisting of amphiphilic polymers with an amide bond, preferably polyacrylamide or poly N-substituted isopropylacrylamide; the pH-sensitive surface modifier is selected from the group consisting of polymers with a carboxyl group and a quaternary ammonium salt, preferably polyacrylic acid, dimethylaminoethyl ester and dimethylaminopropyl methacrylate.

According to certain embodiments of the present invention, the crosslinking agent comprises 3-(methacryloyloxy)propyltriethoxysilane, divinylbenzene, diisocyanate or N,N-methylenebisacrylamide, and the initiator comprises 3-chloropropionic acid, CuCl, 4,4'-dinonyl-2,2-bipyridine or potassium persulfate.

The second aspect of the invention provides a method of preparing the nanoparticle, comprising the steps of: a) preparing the nanoparticle core using the magnetic material; and b) forming the nanoparticle shell by in situ linking the surface modifier monomer to the nanoparticle core by the initiator and/or crosslinking agent. As used herein, "in situ" means that the surface modifier is directly attached to the surface of the nanoparticle core. The resulting modified nanoparticle has a size between 50 nm and 5000 nm, which varies according to different conditions.

According to some embodiments of the present invention, the nanoparticle core is composed of $Fe_3O_4$, $MnFe_2O_4$, $\gamma$-$Fe_2O_3$, or other nanoscale-sized ferrite particles, and these ferrite particles are prepared by the following steps:

dissolving a proportion of the metal salt-containing material in water;

feeding nitrogen to expel oxygen in the solution;

adding a catalyst at a room temperature of 20-30° C. to adjust the pH to 8-12, preferably 10;

keeping agitation and reaction for 20-40 minutes; and reacting under condition of 50-100° C., preferably 70° C. water bath, for 20-40 minutes, then separating with a magnet and drying to obtain the magnetic nanoparticle core.

In a particular embodiment of the present invention, the oxygen-containing metal salt is $FeCl_3 \cdot 6H_2O$ and $FeCl_2 \cdot 4H_2O$, which are dissolved in water in a molar ratio of 15% to 85%, preferably 1:2.5 to 1.5:1, wherein the catalyst is aqueous ammonia. $Fe_3O_4$ nanoparticles can be obtained by following the above steps.

According to some embodiments of the present invention, the step b) comprises dispersing the prepared nanoparticles in an aqueous solution, adding with an xylene solution of 3-chloropropionic acid, polystyrene, CuCl and 4,4'-dinonyl-2,2-bipyridine, wherein the molar ratio between the solution of iron particles and the reaction solution is 1:1; reacting the mixture for 15-30 hours, preferably 24 hours, at 130° C. under continuous agitation; and collecting the nanoparticles with a magnet, washing repeatedly with toluene to obtain hydrophobic polystyrene-wrapped magnetic iron oxide nanoparticles.

According to some embodiments of the present invention, the step b) comprises dissolving and dispersing the resulting nanoparticle core into xylene, adding with a silane coupling agent, wherein the silane coupling agent, wherein the nanoparticles, xylene and silane coupling agent are added in a ratio of 95:5; reacting under the protection of nitrogen atmosphere at 20-100° C., preferably at 80° C., for 2-5 hours, preferably for 3 hours; washing with an alcoholic solvent (preferably absolute ethanol) and drying for 12 hours, dispersing in an aqueous solution under ultrasonic condition, adding with potassium persulfate; reacting under nitrogen protection, at 40-80° C. for 10 minutes, adding with acrylic acid to continue reaction at 40-80° C. for 1 hour, wherein the reaction temperature is preferably 70° C.; and separating with a magnet, washing and drying to obtain the polyacrylic acid-modified hydrophilic nanoparticles.

According to some embodiments of the present invention, the above step b comprises: dissolving and dispersing $Fe_3O_4$ nanoparticles into xylene, and adding with a silane coupling agent, wherein the silane coupling agent (the ratio of the $Fe_3O_4$ nanoparticles and the silane coupling agent as added is 95:5); reacting under protection of nitrogen atmosphere at 80° C. for 2-5 hours, preferably for 3 hours; washing with an alcoholic solvent (preferably absolute ethanol) and drying for 12 hours, dispersing in an aqueous solution under ultrasonic condition, adding with potassium persulfate; reacting under nitrogen protection at 40-80° C. for 10 minutes, adding with a photosensitive monomer such as vinyl benzophenone, a thermosensitive monomer such as N-isopropylacrylamide, or a pH-sensitive monomer such as dimethylaminopropyl methacrylate, etc. (or a blended monomer of acrylic acid and styrene), reacting continuously for 1 hour at 40-80° C., preferably at 70° C.; and separating with a magnet, washing and drying to obtain the photosensitive, thermosensitive or pH sensitive functional monomer-modified magnetic nanoparticles, respectively.

In certain embodiments of the present invention, the photosensitive monomer modification based on the hydrophilic surface modification comprises: dissolving and dispersing the polyacrylic acid-modified magnetic nanoparticles in an alcoholic solvent, dispersing for 5-30 minutes under ultrasonic condition, then adding an initiator and a photosensitive monomer polyvinylbenzophenone, refluxing and reacting at agitation and 130° C. for 24 hours under condition that oxygen is kept out to prepare the photosensitive monomer-modified magnetic nanoparticles.

In the above-mentioned embodiment, when aqueous ammonia is used as catalyst to prepare the nanoparticles, the method for dropping aqueous ammonia is performed in a continuous and dropwise manner with assistance of an electronic pump at a speed of 20-100 drops/minute, preferably 40-60 drops/minute; and when the magnetic material is an element material, the liquid monomer is added in a dropwise and continuous manner with assistance of an electronic pump, and the reaction is carried out under agitation with a speed of 100-1000 rpm, preferably 500-700 rpm.

It should be noted here that the particle size, distribution and morphology (such as a shape of sphere, rod, diamond) of the obtained magnetic nanoparticle core can be relatively easily controlled under the synthetic methods and preparation conditions as we designed above. Furthermore, the surface-modified magnetic nanoparticles prepared by the above method have particle size and distribution superior to those of magnetic nanoparticles obtained by conventional preparation methods. As shown in the following table, the dispersibility index of the obtained nanoparticles (PD.I.) is basically close to 1.0, which clearly shows that the particle size distribution of the obtained particles is narrow. This is very important because, for in vivo biomedical applications, the size and dispersion of nanoparticles determine the breadth of their medical applications. The PD.I described herein for describing the dispersibility of nanoparticles is defined as follows:

$$PD.I.=<Rh^2>/<Rh>^2$$

wherein, Rh represents hydrodynamic radius of particle.

The nanoparticle core and the surface-modified magnetic nanoparticle have distribution PD.I. as shown in the following table:

|  | Magnetic nanoparticle core | After surface modification |
|---|---|---|
| Diameter/nm | 40-50 | 80-100 |
| PD.I./a.u. | 0.005 | 0.0055 |

In addition, as shown in FIG. 2, the structure of the nanoparticles obtained in the present invention is clear.

According to the third aspect of the present invention, there is provided a device for stone removal, which can be used to remove urinary stones in the urinary system more thoroughly, efficiently and safely, and consists of magnetic nanoparticles in combination with a magnetic target separation instrument. The device for stone removal comprises the above-mentioned nanoparticles of the present invention and magnetic target separation instrument for facilitating stone removal. The magnetic target separation instrument can be used for removing stones in urinary system such as kidney stones, ureteral stones and bladder stones, as well as removing stones in human biliary system and stone-like particles in other organs.

Specifically, the magnetic target separation instrument comprises a handle, a flexible rod, a magnetic field source, a magnetically permeable material section, etc. The handle may be provided with an AC or DC power supply, a power switch, a DC battery chamber and an AC plug. The flexible rod is made of a polymer material including, for example, PU, TPU, PE, PVC, NYLON, PEBAX and silicone rubber and the modified materials of the above materials. The magnetic field source made of a permanent magnet or electromagnet can be embedded in the flexible rod, and optionally a high performance magnetically permeable material is connected to the magnetic field source to form a flexible magnetic target separation instrument with different configurations. For example, the permanent magnet is disposed in the middle or back end of the flexible rod, and the magnetically permeable material is disposed in the distal end of the flexible rod. Such a configuration is more useful for the treatment of renal stones under ureteroscope to avoid the situation that the distal end of the flexible rod becomes rigid due to the rigid structure of the permanent magnet or the electromagnet, so that such magnetic target separation instrument can be successfully inserted into the working channel of ureteroscope, and inserted into upper, middle and lower kidney calices to carry out stone removal operation when driven by the ureteroscope.

In one embodiment, the present invention provides a magnetic target separation instrument, which comprises a magnetic end, a connecting rod and a handle; wherein a distal end of the connecting rod is connected to the magnetic end, a proximal end of the connecting rod is connected with the handle; and wherein the connecting rod is made of a material with a certain flexibility. For example, the connecting rod may be composed of a structure of a tube, a wire, a spring tube, a hypotube, a braid tube that is made of a polymer material or a metal material, as well as combinations formed by splicing or nesting the above structures or forms. The connecting rod has a diameter between 0.5 mm and 5 mm. Depending on the method of use, one skilled in the art can choose different diameters for the connecting rod. For example, when the magnetic target separation instrument according to the present invention is introduced into the human body through an endoscope working channel, the diameter of the connecting rod is preferably 0.5 mm to 1.2 mm. Alternatively, when the magnetic target separation instrument according to the present invention is introduced into the human body through the ureteral sheath, the diameter of the connecting rod is preferably 1 mm to 4.5 mm. As an embodiment, when the diameter of the connecting rod is greater than 1 mm, the connecting rod may be a hollow structure, through which a metal wire, a cable, a cord, a catheter, an optical fiber, and any combination of the above can pass, respectively.

In one embodiment, the magnetic end is a magnetic component, and the magnetic component may be a permanent magnet or a soft magnet made of a magnetic material, wherein the magnetic material includes, but not limited to, an alloy magnetic material, a ferrite magnetic material and an intermetallic compound magnetic material, such as: aluminium-nickel-cobalt, iron-chromium-cobalt, iron-cobalt-vanadium, barium ferrite, strontium ferrite, neodymium-iron-boron, samarium-cobalt, manganese-bismuth and other materials. The handle is connected to the magnetic end through the connecting rod, wherein the handle is used for controlling the magnetic end to enter or leave the endoscope channel.

Alternatively, the above-mentioned magnetic component may be made of an electromagnet, and the electromagnet is made of a cable-wound coil. Further, as the inner core, a magnetically permeable material for enhancing magnetic field strength may be added to the cable-wound coil, and the magnetically permeable material includes, but is not limited to, pure iron, ferrite soft magnetic material, iron-nickel alloy, ferrosilicon alloy, vanadium-iron-vanadium alloy, nanocrystalline soft magnetic materials, amorphous soft magnetic materials. The handle is connected to the magnetic end through the connecting rod, wherein the handle is characterized in that the handle is provided with an AC plug or a DC battery chamber for supplying power to the electromagnet. Further, the handle is provided with a power switch for controlling whether the electromagnet is electrified or not. Further, the handle is provided with a regulating switch for adjusting the magnitude of the current so as to adjust the magnetic field strength of the electromagnet.

Alternatively, the above-mentioned magnetic component may be composed of a magnetic field source and a high-efficiency magnetically permeable end. The magnetic field source may be made of a permanent magnet, a soft magnet and an electromagnet. The high-efficiency magnetically permeable end is joined the distal end of the magnetic field source and is used to guide, extend, derive, disperse and cross-link the magnetic field produced by the magnetic field source with no loss or low loss, so as to compensate the simplicity in terms of surface area, volume, shape, flexibility and strength of the magnetic end which are caused by the relatively simple type of the magnetic field source, to better adapt to the human blood vessels, urinary system and other anatomical structures, and to ultimately realize the separation of magnetic targets under a complex and volatile environment. The high-efficiency magnetically permeable end material includes, but is not limited to, pure iron, low carbon steel, ferrosilicon alloy, ferroaluminum alloy, sendust, ferronickel alloy, iron-cobalt alloy, soft magnetic ferrite, amorphous soft magnetic alloy, ultra-crystalline soft magnetic alloy and other materials. The handle is connected to the magnetic end through the connecting rod, wherein the handle is used for controlling the magnetic end to enter or leave the endoscope channel.

In one embodiment, the shape of the magnetic end may be made into a column shape. Still further, the cross-sectional shape of the magnetic end in column shape includes, but is not limited to, round shape, oval shape, polygon shape, radial shape, cross shape, I-shape, petal shape, annular shape, U-shape, porous shape, spiral shape, torsion shape, coiled shape, twisted shape and other shapes. The shape of the magnetic end may be made into a reticulum shape. Further, the reticulated magnetic end may be woven from a single- or multi-stranded magnetic or magnetically permeable materials, and its shape can be woven reticulum shape, coiled reticulum shape, knotted rope reticulum shape, hollow mesh, radial reticulum shape, convergent reticulum shape, cross-section asymmetric reticulum shape, open reticulum shape, pocket-type reticulum shape, spiral-type reticulum shape, barrel-shaped reticulum shape, spindle-shaped reticulum shape, umbrella-shaped reticulum shape, drop-shaped reticulum shape, funnel-shaped reticulum shape, broom-shaped reticulum shape, disorderly entangled reticulum shape. Furthermore, the wire surface or the woven reticulum surface of the reticulated magnetic end can be coated with a biocompatible material such as Teflon, parylene, polyurethane, thermoplastic polyurethane. Still further, the surface of the reticulated magnetic end may be coated with a magnetic material or a material having a high magnetic permeability ($\mu>1$). The handle is connected to the magnetic end through the connecting rod, wherein the handle is used for controlling the magnetic end to enter or leave the endoscope channel.

In one embodiment, the magnetic end is a magnetic component, wherein the magnetic component may be composed of a magnetic field source and a high-efficiency magnetically permeable end. Further, in the magnetic component, the magnetic field source is joined to the high-efficiency magnetically permeable end axially along the axis of the connecting rod, or the magnetic field source is coated by the high-efficiency magnetically permeable end. Still further, there exists a relative movement between the magnetic field source and the high-efficiency magnetically permeable end. In the case that there exists a certain relative movement between the magnetic field source and the high-efficiency magnetically permeable end, an axial rigid rod or rigid tube is connected to the magnetic field source, the rigid rod or the rigid tube passes through the lumen of the connecting rod and the other end is fixed on a control push-rod of the handle, the relative distance between the magnetic field source and the high-efficiency magnetically permeable end can be changed by pushing the control push-rod so as to adjust the magnetic field intensity in the high-efficiency magnetically permeable end. After the magnetic target separation instrument provided by the invention collects, adsorbs and removes magnetic targets, the function can fulfill the quick removal of the magnetic targets from the instrument so as to prepare the instrument for re-entering the human body. The handle is connected to the magnetic end through the connecting rod, wherein the handle is used for controlling the magnetic end to enter or leave the endoscope channel. Further, the handle is provided with a control push-rod, which is connected to the magnetic field source in the magnetic end through an axial rigid rod or rigid tube. Further, the rigid rod or the rigid tube passes through the lumen of the connecting rod and is slidingly disposed in the connecting rod; the relative distance between the magnetic field source and the high-efficiency magnetically permeable end can be changed by pushing and pulling the control push-rod so as to change the adsorption strength of the magnetic end to the magnetic target, to make it possible to quickly separate the magnetic targets from the surface of the magnetic end in vitro, thereby facilitating the re-entry of the instrument into the human body to collect, adsorb and remove the magnetic targets.

Alternatively, the magnetic target separation instrument includes a magnetic end, and the magnetic end contains a steel wire or cord for driving the magnetic end to bend. Further, there are optionally one or two or more pieces of the steel wire or cord. The steel wire or cord is within the magnetic end at one end of the steel wire or cord, passes through the lumen of the connecting rod, and is fixed on an angel adjustment shaft of the handle part at the other end of the steel wire or cord, so that by manipulating the angle adjustment shaft, the magnetic end can be controlled to bend at an angle away from the axial direction of the connecting rod. The handle is connected to the magnetic end through the connecting rod, wherein the handle is used for controlling the magnetic end to enter or leave the endoscope channel. Further, the handle is provided with an angle adjustment shaft, wherein the angle adjustment shaft pulls the magnetic end via one or two or more pieces of steel wire or cord passing through the connecting rod, so that the magnetic end can bend at an angle away from the axial direction of the connecting rod to adapt to the purpose for separating the magnetic targets from different body cavities under complicated environments.

Alternatively, the magnetic target separation instrument includes a magnetic end, the magnetic end is integrated with an image acquisition module. Further, the image acquisition module comprises a lens and a CCD, or comprises a lens and a CMOS, or comprises a lens and an image transmission fiber, or comprises only an image transmission fiber. Preferably, the image acquisition module is composed of a lens and a CMOS. Further, the magnetic end with the image acquisition module includes a steel wire or cord for driving the magnetic end to bend, wherein the steel wire or cord is fixed within the magnetic end at one end of the steel wire or cord, passes through the lumen of the connecting rod, and is fixed on an angel adjustment shaft of the handle part at the other end of the steel wire or cord; by manipulating the angel adjustment shaft, the magnetic end can be controlled to bend at an angle away from the axial direction of the connecting rod. The handle is connected to the magnetic end through the connecting rod, wherein the handle is used for controlling the magnetic end to enter or leave the endoscope channel. Further, the handle is provided with an angle adjustment shaft, wherein the angle adjustment shaft pulls the magnetic end via one or two or more pieces of steel wire or cord passing through the connecting rod, so that the magnetic end can bend at an angle away from the axial direction of the connecting rod to adapt to the purpose for separating the magnetic targets from different body cavities under complicated environments. Further, the handle is provided with an interface for transmission of video image signal to connect an external video display device so as to facilitate monitoring the surgical field and process recording. The external video display device belongs to the prior art and is not included in the content of the present invention, and thus its details are not described herein.

In the present invention, the connection relationship between the magnetic end and the connecting rod is that the magnetic end is sheathed on the distal end of the connecting rod, or the connecting rod passes through the magnetic end, or the connecting rod and the magnetic end are connected by bonding, or the connecting rod and the magnetic end are connected by covering with a same material, or the connecting rod and the magnetic end are connected by metal crimping, or the connecting rod and the magnetic end are connected by a quick connecting mechanism, wherein the quick connecting mechanism includes, but not limited to, a screw thread, a Luer taper, a snap joint, a screw buckle, a socket component, a plug-in component, a magnetic component, an interference fit component and so on that can achieve quick connection.

The method for using the magnetic target separation instrument according to the present invention is as follows: 1) firstly, the stones in a body are crushed by means of a traditional lithotripsy; 2) functional materials with magnetic properties (for example, but not limited to, the nanoparticles of the present invention) are injected into the region containing the crushed stones through the endoscope working channel; 3) the magnetic functional material has a physical or chemical interaction on the surface of the stones and wraps the surface of the stones so as to finally magnetize the stones; 4) the magnetic target separation instrument is introduced to gather the magnetized stones together in the front end of the instrument by the magnetic field of the magnetic end, and finally the gathered stones together with the instrument are removed from the body to fulfill the purpose of gathering stones in non-contact mode and bulk removal of stones at a high efficiency.

In the forth aspect of the invention, there is provided a use of the nanoparticles of the present invention in manufacture of an article, in which the nanoparticles are prepared in the form of a solution or powder.

The invention provides a novel preparation process for synthesizing hydrophilic, hydrophobic, thermosensitive and pH-sensitive as well as photosensitive magnetic nanoparticles, which has the advantages of simple preparation process, good repeatability and convenient application. By the hydrophobic interaction between the prepared hydrophobic nanoparticles and stones, the chemical bond interaction between hydrophilic nanoparticles and stones, and the polymerization of the photosensitive nanoparticles under illumination, the stones are wrapped; and the thermosensitive and pH-sensitive nanoparticles can wrap stones through physically wrapping action in ureter; thereby, small stones remaining in body can be removed quickly without damage from the body under the action of an externally applied magnetic field, that is, the stones can be drawn and moved without injuring ureteral wall, and meanwhile be disposed conveniently without easy shift.

The present invention is further described with reference to the accompanying drawings.

SPECIFIC MODELS FOR CARRYING OUT THE INVENTION

Figure 1:
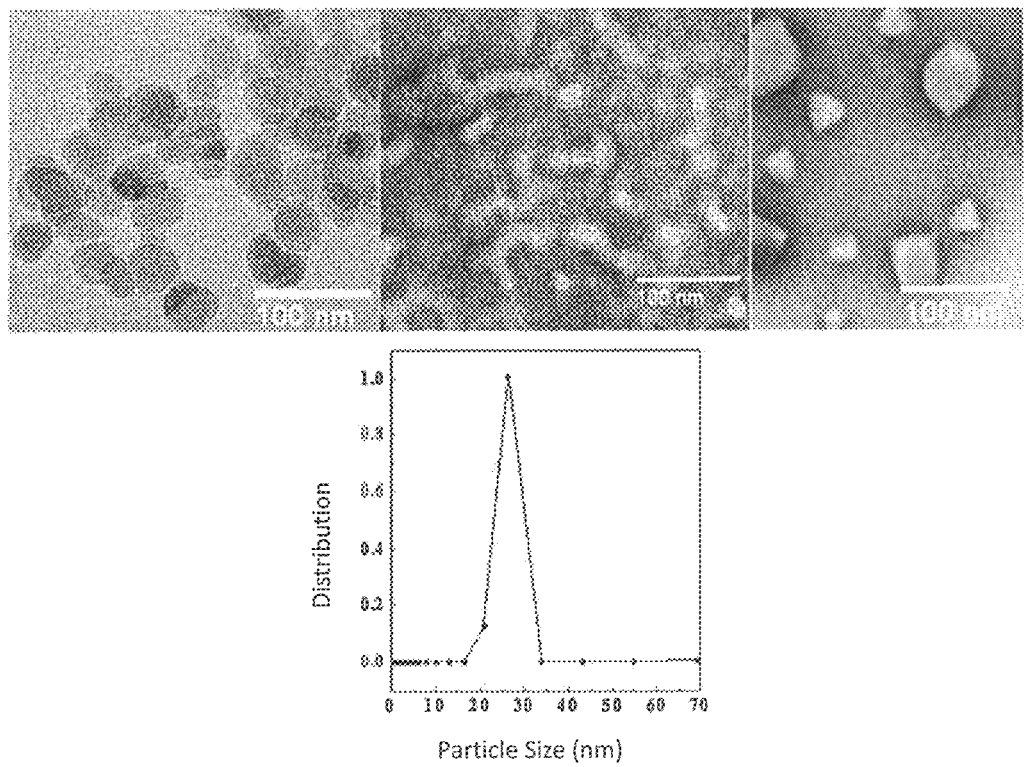
FIG. 1 shows the transmission electron microscope (TEM) images and the particle size distribution diagrams under dynamic light scattering for the cores with different morphologies obtained in Example 1 of the present invention; upper, left: sphere shape; middle: rod shape; right: diamond shape; lower, particle size distribution.
Figure 2:
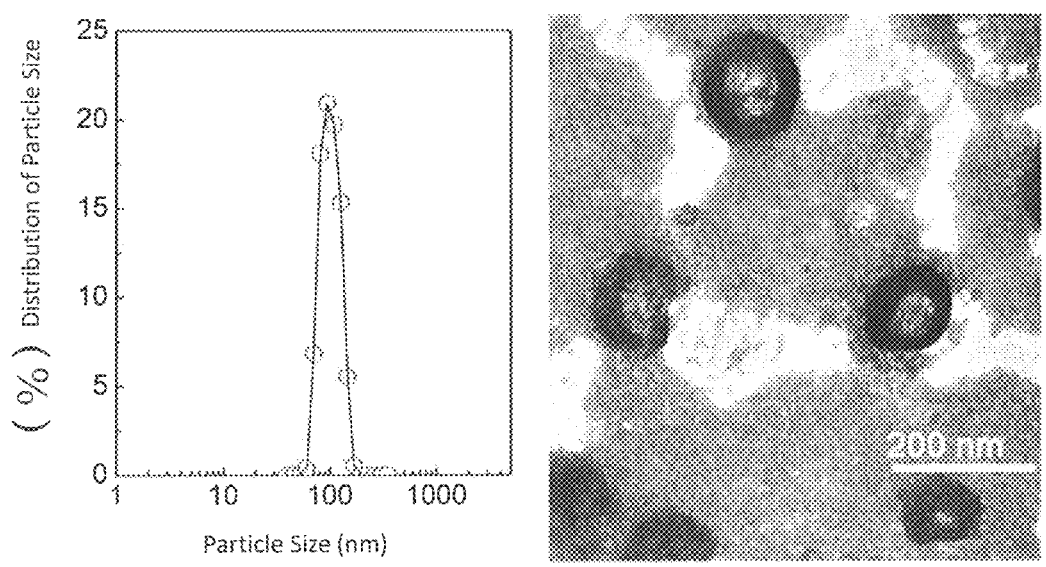
FIG. 2 shows the particle size distribution diagram under dynamic light scattering for the monomer-modified nanoparticles obtained in Example 4 of the present invention; and TEM images of the monomer-modified nanoparticles obtained in Example 3 of the present invention; left: Particle size distribution diagram; right: TEM diagram.
Figure 3:
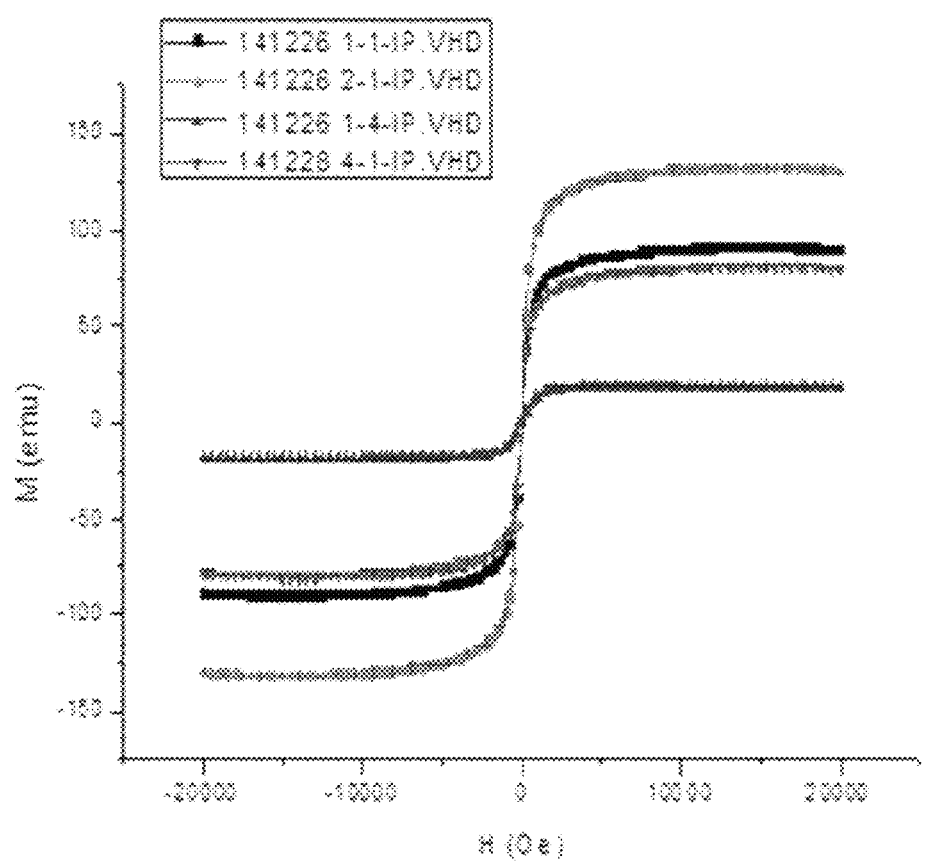
FIG. 3 shows the hysteresis curves of the monomer-modified nanoparticle cores with different $Fe^{3+}/Fe^{2+}$ ratios in the synthesis of the nanoparticles obtained in Example 3 of the present invention.
Figure 4:
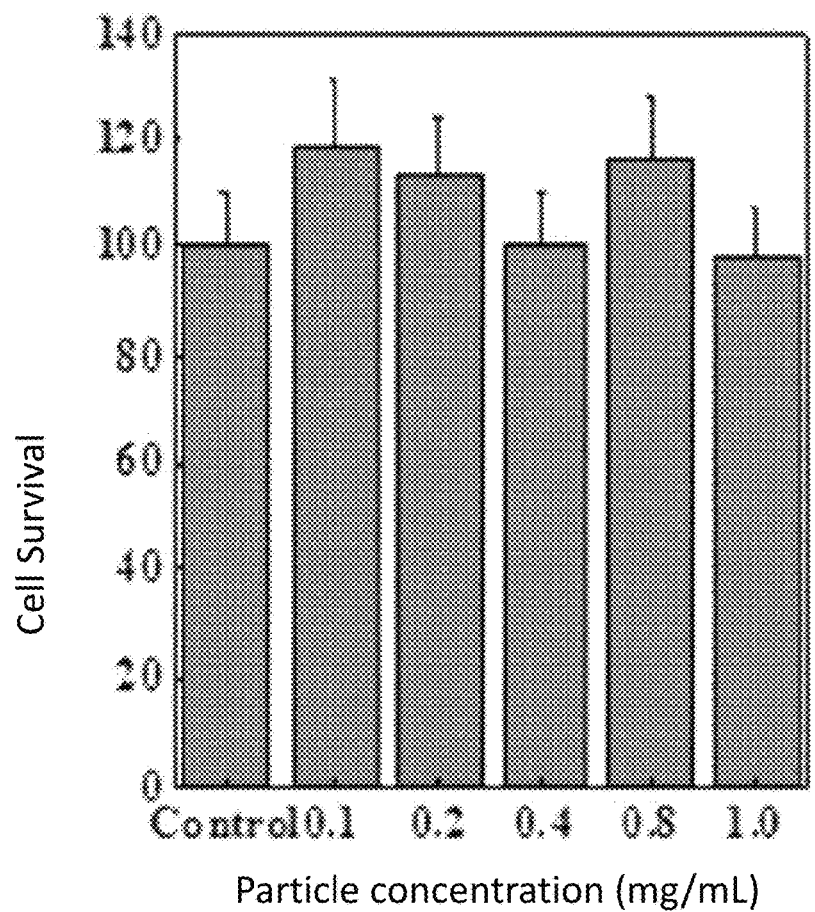
FIG. 4 shows a graph of biocompatibility to 293T cells for the functional magnetic nanoparticles obtained in Example 4 of the present invention.

The present invention is further illustrated below with reference to the accompanying drawings and specific examples. It should be understood that the following examples are only used to illustrate the present invention, rather than to limit the scope of the present invention.

According to a first aspect of the present invention, there is provided a magnetic nano-material capable of safely and efficiently removing stones in urinary system. The present invention provides a functional magnetic nanoparticle, comprising: hydrophilic, hydrophobic, photosensitive, thermosensitive, pH-sensitive magnetic nanoparticles, which morphology can be spherical, rod-shaped and the like, which structure can be of core-shell structure consisting of a magnetic core and a monomer modifier such as hydrophilic, hydrophobic, temperature sensitive, pH-sensitive or photosensitive surface modifiers as well as a small amount of initiator; in which the hydrophilic surface modifier forms a hydrophilic shell by polymerization to wrap the magnetic nanoparticle core, including the hydrophilic materials with positive charges, negative charges and electricity neutrality; the hydrophobic surface modification is carried out by a poor water-soluble polymer or inorganic material; the other functional materials such as photosensitive, thermosensitive and pH-sensitive monomer modifiers may be polymerized by a crosslinking agent and embedded in a hydrophobic shell, or these monomer modifiers may be in situ and directly attached to the surface of the core by an initiator and/or crosslinking agent.

Among the various kinds of responsive magnetic nanoparticles such as hydrophilic, hydrophobic, thermosensitive, pH-sensitive and photosensitive magnetic nanoparticles, the materials for synthesizing magnetic nanoparticle cores comprise $Fe^{3+}$, $Fe^{2+}$ and $Mn^{2+}$, $Ni^{2+}$ compounds, as well as metal elements such as iron (Fe), nickel (Ni), copper (Cu), cobalt (Co), platinum (Pt), gold (Au), europium (Eu), gadolinium (Gd), dysprosium (Dy), terbium (Tb), or composites and oxides of the metals, such as $Fe_3O_4$ or $MnFe_2O_4$, preferably iron, manganese or their compounds, also preferably, any one of them or any combination of two or more of them may be used; and the core has a size of 2-50 nm.

The preparation method of the magnetic nanoparticle core includes co-precipitation methods, emulsion methods, redox reaction or high-temperature high-pressure methods. The weight percentage of the magnetic nanoparticle core accounts for 30% to 95% relative to the total weight of the functional magnetic nanoparticle, taking the synthesis of $Fe_3O_4$ as example, the ratio of $Fe^{3+}$ to $Fe^{2+}$ is 15% to 85%, preferably 1:2.5 to 1.5:1 for $Fe^{3+}$ and $Fe^{2+}$.

The surface of the magnetic nanoparticle can be subjected to functional modification, such as hydrophilic modification, hydrophobic modification, and modification with photosensitive, thermosensitive and pH-sensitive materials.

According to a first embodiment of the present invention, there is provided a hydrophilically modified functional particle, wherein the core size is 2-50 nm, the magnetic nano-core has a weight of 30-95% relative to the total nanoparticle; the hydrophilic surface modifier is a polycationic or an anionic polymer, such as acrylic acid, methacrylic acid and isobutyl acrylamide, etc., which weight percentage is 2-8% relative to the whole hydrophobic magnetic nanoparticle. The magnetic core particle is attached on its surface with an initiator such as 3-chloropropionic acid or the like, then a polymer based on acrylic acid, methacrylic acid and isobutyl acrylamide or the like is modified on the particle surface with a crosslinking agent by a chemical reaction, such as radical, ring-opening polymerization and atom transfer radical polymerization (ATRP); the shape of the particle may be spherical, rod-shaped and layered, preferably spherical particles. The crosslinking agent is 3-(methacryloyloxy) propyltriethoxysilane (MPS), divinylbenzene and diisocyanate or N,N-methylenebisacrylamide (MBA) and the like.

According to a second embodiment of the present invention, there is provided a hydrophobically modified functional particle, wherein the core has a size of 2-50 nm, the magnetic nano-core is 30-95% by weight relative to the whole nanoparticle; the hydrophobic surface modifier is an water insoluble monomer, such as olefins, for example, polystyrene and the like, which weight percentage is 2-8% by weight relative to the whole hydrophobic magnetic nanoparticle. The magnetic core particle is attached to its surface with an initiator such as 3-chloropropionic acid, and then a hydrophobic polymer based on styrenes is modified on the particle surface by a crosslinking agent via a chemical reaction such as radical, ring-opening polymerization and atom transfer radical polymerization (ATRP); the morphology of the particle may be spherical, rod-shaped and layered, preferably spherical particle. The crosslinking agent is 3-(methacryloyloxy) propyl triethoxysilane (MPS), divinylbenzene and diisocyanate or N,N-methylenebisacrylamide (MBA) and the like.

According to a third embodiment of the present invention, there is provided a photosensitive surface-modified functional particle, wherein the core has a size of 2-50 nm, and the magnetic core is 30-95% by weight relative to the whole nanoparticle; the photosensitive modifier is selected from the group consisting of azos and quinolines as well as benzophenones (PVBP), etc., which weight percentage is 2-8% relative to the whole hydrophobic magnetic nanoparticle. The magnetic core particle is attached to its surface with an initiator such as 3-chloropropionic acid, and then a photosensitive polymer based on benzophenone (PVBP) and the like is modified to the surface of the particle by a crosslinking agent via a chemical reaction such as radical, ring-opening polymerization and atom transfer radical polymerization (ATRP); the morphology of the particle may be spherical, rod-shaped and layered, preferably spherical particle. The crosslinking agent is 3-(methacryloyloxy) propyltriethoxysilane (MPS), divinylbenzene and diisocyanate or N,N-methylenebisacrylamide (MBA) and the like.

According to a fourth embodiment of the present invention, there is provided a thermosensitive surface-modified functional particle, wherein the size of the core is 2-50 nm, and the magnetic nano-core is 30-95% by weight relative to the whole nanoparticle; the thermosensitive surface modifier is selected from the group consisting of amphiphilic polymers carrying amide bonds, such as polyacrylamide, poly N-substituted isopropylacrylamide, etc., which weight percentage is 2-8% relative to the whole hydrophobic magnetic nanoparticle. The magnetic core particle is attached to its surface with an initiator such as 3-chloropropionic acid, and then a thermosensitive polymer such as poly N-substituted isopropylacrylamide is modified to the surface of the particle by a crosslinking agent via a chemical reaction such as radical, ring-opening assembly and atom transfer radical polymerization (ATRP); the shape of the particle may be spherical, rod-shaped and layered, preferably spherical particle. The crosslinking agent is 3-(methacryloyloxy) propyltriethoxysilane (MPS), divinylbenzene and diisocyanate or N,N-methylenebisacrylamide (MBA) and the like.

According to a fifth embodiment of the present invention, there is provided a pH-sensitive surface-modified functional particle, wherein the core has a diameter of 2 to 50 nm, the magnetic nano-core is 30 to 95% by weight relative to the whole nanoparticle; the pH-sensitive surface modifier is selected from the group consisting of polymers carrying carboxyl groups and quaternary ammonium salt groups, such as polyacrylic acid, dimethylaminoethyl ester and dimethylaminoethyl methacrylate, etc., which weight percentage is 2-8% relative to the whole hydrophobic magnetic nanoparticle. The magnetic core particle is attached to its surface with an initiator such as 3-chloropropionic acid, and then a pH-sensitive polymer based on dimethylaminoethyl methacrylate and dimethylaminoethyl methacrylate or the like is modified to the surface of the particle by a crosslinking agent via a chemical reaction such as radical, ring-opening polymerization and atom transfer radical polymerization (ATRP); the shape of the particle may be spherical, rod-shaped and layered, preferably spherical particle. The crosslinking agent is 3-(methacryloyloxy) propyltriethoxysilane (MPS), divinylbenzene and diisocyanate or N,N-methylenebisacrylamide (MBA) and the like.

In the above embodiments of the present invention, an initiator and/or a crosslinking agent are further included. The initiator comprises initiators such as thermal initiators, for example, potassium persulfate, ammonium persulfate and azo type initiators; the crosslinking agent comprises 3-(methacryloyloxy) propyltriethoxysilane (MPS), divinylbenzene and diisocyanate or N,N-methylenebisacrylamide (MBA), molecular weight is 100,000, and oleic acid, etc.

According to a second aspect of the present invention, there is provided a preparation method for a nanoparticle. The preparation method generally comprises two main steps: synthesis of a magnetic nanoparticle core, and various surface modifications based on the magnetic nanoparticle core (hydrophilic, hydrophobic and thermosensitive, photosensitive and pH-sensitive modification). Taking the preparation of magnetic $Fe_3O_4$ nanoparticles as an example, the two steps of the preparation method are respectively described in detail.

1) Preparation of Magnetic $Fe_3O_4$ Nanoparticle Core $FeCl_3.6H_2O$ and $FeCl_2.4H_2O$ in a certain molar ratio (the molar ratio of $FeCl_3.6H_2O$ and $FeCl_2.4H_2O$ is 15% to 85%, preferably 1:2.5 to 1.5:1) are dissolved in 100 mL of water, fed with nitrogen gas to expel oxygen in the solution, added with aqueous ammonia at a room temperature of 20-30° C. to adjust the pH value of 8-12, preferably 10, and kept agitation and reaction for 20-40 minutes; then under a 50-100° C., preferably 70° C. water bath, the reaction is carried out for 20-40 minutes, and then $Fe_3O_4$ nanoparticles are obtained by separation with a magnet and drying. There are different kinds of preparation methods such as co-precipitation method, thermal decomposition method, hydrothermal synthesis method, microemulsion method (reverse micelle method) and the like.

2) Surface Modification of the Synthesized $Fe_3O_4$ Nanoparticle Core 2.1) Hydrophobic Modification of the Surface of the Synthesized $Fe_3O_4$ Nanoparticle Core The $Fe_3O_4$ nanoparticle core prepared in the step 1) is dispersed into an aqueous solution, added with an initiator 3-chloropropionic acid and pre-treated for 12 hours, then added with an xylene solution of a hydrophobic surface-modifying monomer polystyrene and an active initiator CuCl and 4,4'-dinonyl-2,2-dipyridine (the molar ratio of the iron particle solution and the reaction solution is 1:1), and the mixture solution is reacted under continuous agitation at 130° C. for 15-30 hours, preferably 24 hours; the resulting nanoparticles are collected with a magnet and washed repeatedly with toluene to obtain the hydrophobic polystyrene-wrapped magnetic iron oxide nanoparticles.

Here, 3-chloropropionic acid is used as an initiator, and CuCl and 4,4'-dinonyl-2,2-bipyridine are used as another initiator. In addition, according to one embodiment of the present invention, the reaction time is preferably 18 to 30 hours, preferably 24 hours. In addition, according to one embodiment of the present invention, the solvent is toluene or xylene in an amount of ½ to 1 of the monomer volume, the mass ratio of the surface-modified polystyrene magnetic nanoparticles, the initiator and the monomer is 95:0.5:4.5.

2.2) Hydrophilic Modification of the Surface of the Synthesized $Fe_3O_4$ Nanoparticle Core The $Fe_3O_4$ nanoparticle core obtained in the above step 1) is dissolved and dispersed into xylene, added with a silane coupling agent (the addition ratio of $Fe_3O_4$ nanoparticles and the silane coupling agent is 95:5), and reacted at 80° C. under nitrogen protection for 2-5 hours, preferably 3 hours; then washed with an alcoholic solvent (preferably absolute ethanol) and dried for 12 h, dispersed in an aqueous solution under ultrasonic condition, added with potassium persulfate; reacted under nitrogen protection at 40-80° C. for 10 minutes, then added with acrylic acid and reacted continuously at 40-80° C. for 1 hour, preferably reacted at a reaction temperature of 70° C.; separated by a magnet, washed and dried to obtain polyacrylic acid-modified, hydrophilic surface-modified magnetic nanoparticles.

Here, the silane coupling agent is 3-(methacryloyloxy) propyl triethoxysilane (MPS) in an amount of 8 to 16 times the mass of acrylic acid; the solvent is benzene or 2-toluene; potassium persulfate is used as initiator; the reaction time is preferably 20 minutes to 80 minutes. According to one embodiment of the present invention, the mass ratio of the surface-modified magnetic $Fe_3O_4$ nanoparticles, the potassium persulfate and the acrylic acid monomer is 25-100:1:100.

In addition, the alcoholic solvent here is methanol, ethanol or butanol, preferably ethanol, the reaction temperature is preferably 100° C. to 150° C., the reaction time is preferably 18 hours to 24 hours, and the mass ratio of the photosensitive monomer-modified magnetic nanoparticles, the potassium sulfate and the vinylbenzophenone monomer is 25-100:1:100.

2.3) Functional Modification of the Surface of the Synthesized $Fe_3O_4$ Nanoparticle Core The $Fe_3O_4$ nanoparticle core as prepared in the above step 1) is dissolved and dispersed into xylene, added with a silane coupling agent (the addition ratio of the $Fe_3O_4$ nanoparticles and the silane coupling agent is 95:5), reacted under nitrogen protection at 80° C. for 2-5 hours, preferably 3 hours, then washed with an alcoholic solvent (preferably absolute ethanol) and dried for 12 hours, dispersed into an aqueous solution under ultrasonic condition, added with potassium persulfate; reacted under nitrogen protection at 40-80° C. for 10 minutes, then added with a photosensitive monomer vinyl benzophenone, or a thermosensitive monomer N-substituted isopropylacrylamide, or a pH-sensitive monomer dimethylaminoethyl methacrylate, reacted at 40-80° C. for 1 hour, preferably reacted at a reaction temperature of 70° C.; separated by a magnet, washed and dried to obtain magnetic nanoparticles with photosensitive, thermosensitive or pH-sensitive surface modification, respectively.

In addition, the functionally modified nanoparticles here may also be obtained by a cross-reaction with steps 2.1 and 2.2) and step 3) after pre-modification of the surface of the nanoparticle in the steps 2.1 and 2.2). That is, after the modification of 3-chloropropionic acid in step 2.1 (or the modification of silane coupling agent in step 2.2), the hydrophobic monomer styrene (or hydrophilic monomer acrylic acid) and the functional monomer such as vinyl benzophenone, N-substituted isopropylacrylamide or dimethylaminoethyl methacrylate and the like are added at the same time, and reacted at 40-80° C. for 1 hour, preferably reacted at a reaction temperature of 70° C.; separated by a magnet, washed and dried to obtain magnetic nanoparticles with photosensitive, thermosensitive or pH-sensitive surface modification. The co-reaction would result in co-modified functional nanoparticles corresponding to polystyrene (or polyacrylic acid) and the functional monomer.

Here, the silane coupling agent is 3-(methacryloyloxy) propyl triethoxysilane (MPS) in an amount of 8 to 16 times the mass of acrylic acid; the solvent is benzene or 2-toluele in an amount of 8 to 16 times the mass of acrylic acid; potassium persulfate is used as initiator; the reaction time is preferably 20 minutes to 80 minutes. According to one embodiment of the present invention, the mass ratio of the surface-modified magnetic $Fe_3O_4$ nanoparticles, the potassium persulfate and the acrylic acid monomer is 25-100:1:100.

In addition, the alcoholic solvent here is methanol, ethanol or butanol, preferably ethanol, the reaction temperature is preferably 100° C. to 150° C., and the reaction time is preferably 18 hours to 24 hours. The mass ratio of the functional monomer-modified magnetic nanoparticles, the potassium persulfate and the functional monomer is 25-100:1:100.

In the process for preparing the nano iron oxide (in step 1), the $Fe_3O_4$ nanoparticles are nanoscale ferroferric oxide particles ($Fe_3O_4$), $MnFe_2O_4$, nanoscale ferric oxide particles ($\gamma\text{-}Fe_2O_3$) or other nanoscale ferrite particles, the aqueous ammonia is used as catalyst, the reaction pH is preferably 9 to 10, the reaction time is preferably 20 to 30 minutes, the reaction temperature is between 50-100° C., preferably 70-80° C., the preferred ratio of $Fe^{3+}:Fe^{2+}$ is 15% to 85%, preferably 1.5:1 to 1:2.5.

In addition, in the above process for preparing nanoscale iron oxide (i.e., step 1)), the nanoparticle core is nanoscale ferroferric oxide particles ($Fe_3O_4$). Those skilled in the art can understand that it is also possible to use $MnFe_2O_4$, nanoscale ferric oxide particles ($\gamma\text{-}Fe_2O_3$) or other nanoscale ferrite particles. The aqueous ammonia is used as catalyst, the reaction pH is preferably 9 to 10, the reaction time is preferably 20-30 minutes, the reaction temperature is between 50-100° C., preferably 70-80° C. The preferred ratio of $Fe^{3+}:Fe^{2+}$ is 15% to 85%, preferably 1:2.5 to 1.5:1.

In addition, in the above embodiments of the present invention, the agitation in the above reaction system is performed by a magnetic stirrer at a speed of 100-1000 rpm, preferably 500-700 rpm.

In addition, in the above embodiments of the present invention, the aqueous ammonia and the liquid monomer are added dropwise continuously and uniformly by an electronic pump at a rate of 20-100 drops/minute, preferably 40-60 drops/minute. Through the use of electronic pump for continuous and uniform dripping, large-scale production can be easily achieved, and the dispersibility and uniformity of nanoparticles can be well controlled.

According to a third aspect of the present invention, there is provided a magnetic target separation instrument for assisting the removal of stone in urinary system. The magnetic target separation instrument comprises a handle 1, a flexible rod 2, a magnetic field source 3, and an optional magnetically permeable material section 4 (in the present invention, the side of the handle is defined as the proximal end of the instrument, and the end of the magnetic field source is defined as the distal end). When an electromagnet is selected as the magnetic field source 3, a switch 11 can be integrated into the handle 1, and the magnetic field power supply can be selected from DC battery, and a battery compartment 12a and a battery cover 13a are provided accordingly, when an AC power is selected as the magnetic field power supply, an AC power plug 12b is provided on the handle correspondingly. When the magnetic field source is an electromagnet, the magnetic field source 3 is composed of an electromagnet core 32a and an electromagnetic coil 33a, and externally provided with a magnetic field source encapsulation membrane 31a made of biocompatible materials; when the magnetic field source 3 is a permanent magnet, the magnetic field source 3 is composed of the permanent magnet 32b and the magnetic field source encapsulation membrane 31b on its surface; in order to ensure the accessibility of the present invention in human body, a magnetically permeable material section 4 can be optionally disposed at the distal end of the magnetic field source 3, that is, when the electromagnet is used as the magnetic field source, the magnetically permeable material section 4a can be optionally disposed at the distal end of the electromagnet 3a, and the magnetically permeable material section is composed of a highly magnetically permeable material 42a and a magnetically permeable material encapsulating membrane 41a, in which the highly magnetically permeable material 42a can be made of an iron-based magnetically permeable material, preferably a pure iron material, and the magnetically permeable material encapsulating membrane 41a and the magnetic field source encapsulation membrane 31a can be made of the same material; when the permanent magnet is selected as the magnetic field source, the magnetically permeable material section 4b may also be disposed at the distal end of the permanent magnet 3b, composed of the highly permeable material 42b and the magnetically permeable material encapsulation membrane 41b, and the magnetically permeable material encapsulation membrane 41b and the magnetic field source encapsulation membrane 31b can be made of the same material; when it is not necessary to dispose a magnetically permeable material section at the distal end of the magnetic field source, the system of the present invention is composed of the handle 1, the flexible rod 2 and the magnetic field source 3; for example, when the permanent magnet is selected as the magnetic field source, the magnetic field source at distal end would be composed of a permanent magnet 32c and an externally disposed magnetic field source encapsulation membrane 31c; in the above embodiment, the flexible rod 2 may be made of a polymer material such as PU, TPU, PE, PVC, NYLON, PEBAX and silicone rubber, as well as modified materials of the above materials, and the magnetic field source encapsulation membranes 31a, 31b and 31c as well as the magnetically permeable material encapsulation membranes 41a and 41b are all made of the same material as the flexible rods.

Further, the present invention provides a use of a magnetic nanoparticle, in which the magnetic nanoparticle is further processed to form a stone-removing solution (using physiological saline, buffer as solvent) or a stone-removing powder, preferably a stone-removing solution, which is used as a medical clinical article.

Figure 12:
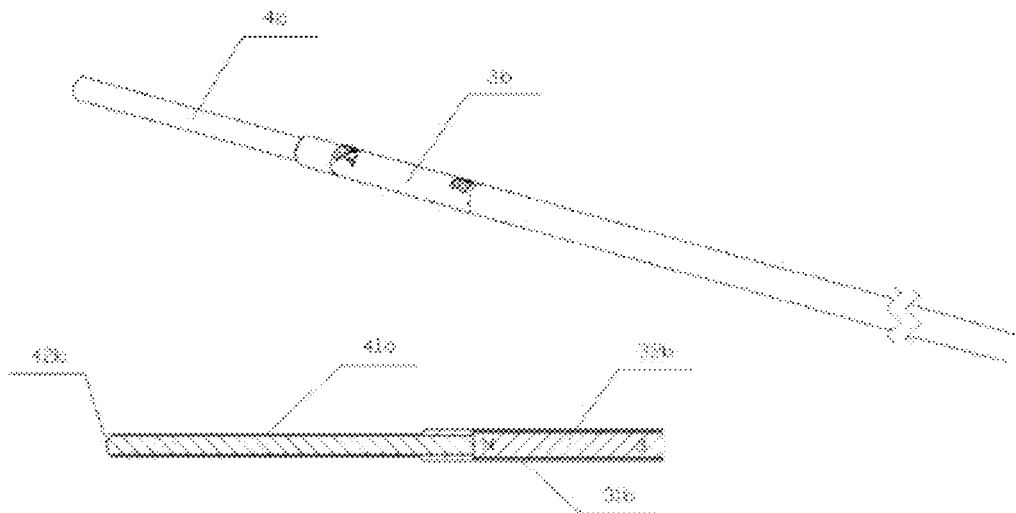
FIG. 12 shows a schematic view of the magnetic target separation instrument of the present invention which uses a permanent magnet as magnetic field source and a magnetically permeable material section at distal end.
Figure 13:
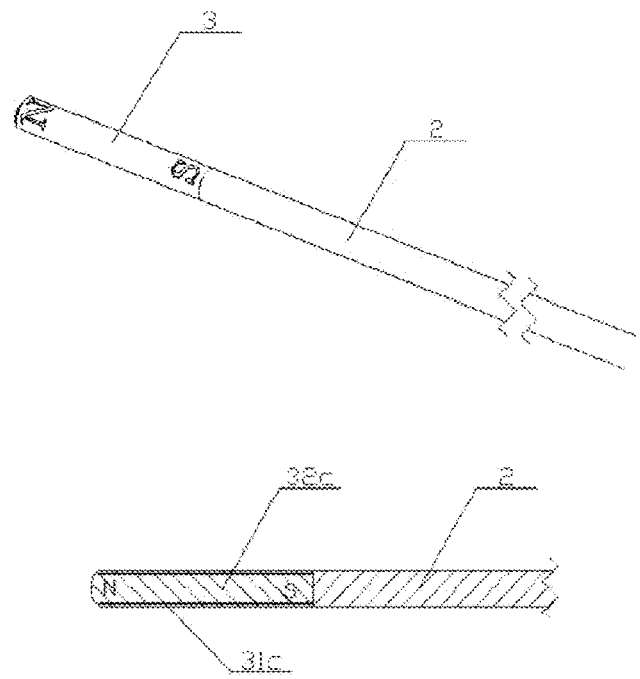
FIG. 13 shows a schematic view of the magnetic target separation instrument of the present invention which uses a permanent magnet as magnetic field source without a magnetically permeable material section at distal end.
Figure 14:
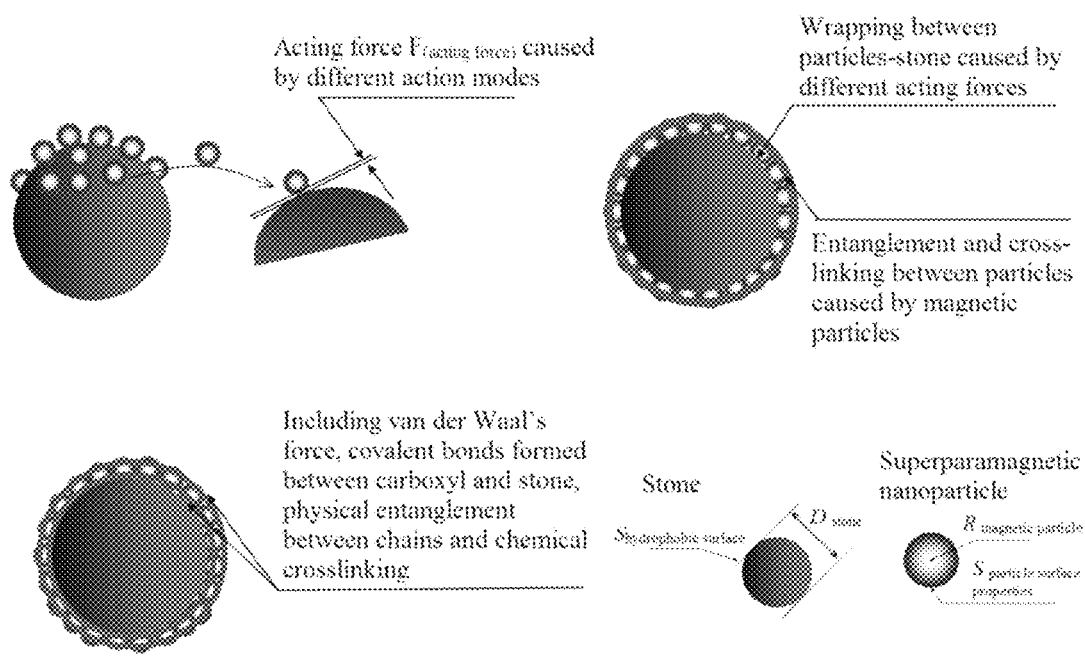
FIG. 14 shows a diagram of the principle of interaction between magnetic particles and stones.

The basic principle of the high performance system for removing a stone in urinary system, which consists of the functional magnetic nanoparticle and the magnetic target separation instrument as shown, is achieved by the following steps: 1) pulverization of stones in vivo; 2) injection of the functional magnetic nanoparticles: 3) interaction between the functional magnetic nanoparticles and the stones; 4) wrapping the stones with the functional magnetic nanoparticles, 5) physical or chemical crosslinking of the magnetic nanoparticles on the surface of the stones; 6) removal of the magnetized stones under the guidance of an external magnetic field. The stones are wrapped and magnetized by the magnetic nanoparticles via physical adsorption, chemical bonding and the like. The physical adsorption mainly refers to an adsorption action generated by van der Waal's force and hydrophobic interaction within the action range between hydrophobic magnetic particles-particles and between particles-stones, so that the surface of the stones are adsorbed and wrapped by the magnetic particles; the chemical bonding mainly refers to the binding action between the hydrophilic magnetic nanoparticles-particles and between particles-stones mainly through the formation of chemical bonds (chemical bonds, such as hydrogen bonds, covalent bonds, etc., between carboxyl on the surface of the particles and the stones), so that the surface of the stones is wrapped with the magnetic particles; the chemical bonding comprises: the functional magnetic nanoparticles (such as photosensitive, thermosensitive nanoparticles, etc.) firstly act on the stones via physical adsorption, and then further enhance the action force between particles-particles and particles-stones via photosensitive crosslinking, thermosensitive physical entanglement (crosslinking) and the like to wrap the stones. The principle of the above action is shown in FIG. 12.

The followings are detailed examples of the structure, preparation and use of the magnetic nanoparticles of the present invention.

Example 1: Preparation of Magnetic Nanoparticle Core

1. Preparation of 10 nm $Fe_3O_4$ by Co-Precipitation Method 3.05 g $FeCl_3.6H_2O$ and 2.08 g $FeCl_2.4H_2O$ (molar ratio 1:1) were dissolved in 50 ml deionized water in a three-necked flask. Nitrogen gas was used throughout the experiment. Aqueous ammonia was added dropwise with a syringe and stirred vigorously at room temperature to adjust pH1 to 9, the solution gradually turned from yellow to brown and finally black, and the reaction was carried out for 20 minutes. After the reaction, the solution was placed in a 70° C. water bath and incubated for 20 minutes, stirred vigorously to remove excess ammonia. The three-necked flask was taken out and allowed to cool to room temperature under vigorous agitation. The suspension of the synthesized $Fe_3O_4$ magnetic particles was poured into a 50 ml centrifuge tube, a powerful magnet was used to attract the magnetic particles, liquid waste was discarded, deionized water was added, the magnetic particles were re-suspended under ultrasonic, so repeatedly to wash away excess ammonia until pH showed neutral. The collected magnetic particles were placed in an oven at 65° C. to be dried and dewatered. The synthesized magnetic particles were weighed, and 1.0 ml suspension of 0.02 mg/ml magnetic particles was formulated for measurement of particle size. A total of 1.5 ml of 0.02M sodium oleate solution was added dropwise to 1.0 ml suspension of 0.2 mg/ml magnetic particles, reacted at 70° C. under nitrogen and vigorous agitation for 30 minutes, and then cooled to room temperature. Excess sodium oleate was removed by dialysis using 12KD dialysis membrane. Thus, 1.0 ml of 0.02 mg/ml sodium oleate-encapsulated $Fe_3O_4$ solution was formulated, and its particle size was measured.

2. Preparation of $Fe_3O_4$ Magnetic Nanoparticle Core 2.1 Thermal Decomposition Method 2.1.1 Synthesis of 4 nm $Fe_3O_4$ Seeds:

5 mmol of ferric triacetylacetonate, 5 mmol of 1,2-dihydroxyhexadecane, 3 mmol of oleic acid, 1 mmol of oleylamine were dissolved in 20 ml of diphenyl ether and magnetically stirred under a nitrogen atmosphere. The above mixture was stirred at 200° C. for 30 minutes, and then heated under reflux for 30 minutes at 265° C. under the protection of nitrogen gas. The heating was stopped, and the dark brown liquid mixture obtained from the reaction was cooled to room temperature; under atmospheric conditions, 400 ml of ethanol was added, and the resulting black material was separated by overspeed centrifugation. The black product obtained by centrifugation was redissolved in n-hexane containing 50 μL of oleic acid and 50 It of oleylamine, centrifuged at 600 rpm for 10 minutes to remove insoluble residues. The resulting 4 nm $Fe_3O_4$ product was precipitated with ethanol, centrifuged at 600 rpm for 10 minutes to remove solvent and then redispersed into n-hexane. The following different methods were used respectively to synthesize surface-functionalized nanoparticles with different sizes.

2.1.2 Synthesis of 6 nm $Fe_3O_4$ Nanoparticle Core Using 4 nm $Fe_3O_4$ Seeds 20 mmol of ferric triacetylacetonate, 10 mmol of 1,2-dihydroxyhexadecane, 6 mmol of oleic acid and 6 mmol of oleylamine were dissolved in 20 ml of diphenyl ether and magnetically stirred under a nitrogen atmosphere. The above mixture was heated at 200° C. for 2 hours, and then heated under reflux for 1 h at 300° C. under the protection of nitrogen gas. The heating was stopped, and the dark brown liquid mixture obtained from the reaction was cooled to room temperature. The aforementioned operation steps for the synthesis of the 4 nm $Fe_3O_4$ particles were adopted to obtain a black brown suspension of 6 nm $Fe_3O_4$ particles dispersed in n-hexane.

2.1.3 Synthesis of 8 nm $Fe_3O_4$ Nanoparticle Core Using 6 nm $Fe_3O_4$ Seeds 2 mmol of ferric triacetylacetonate, 10 mmol of 1,2-dihydroxyhexadecane, 2 mmol of oleic acid and 2 mmol of oleylamine were dissolved in 20 ml of ethyl ether and magnetically stirred under nitrogen protection. 84 mg of 6 nm $Fe_3O_4$ particles were weighed, dissolved in 4 ml of n-hexane, and then added to the above mixture liquid. The above mixture liquid was first heated at 100° C. for 30 minutes to remove n-hexane, then heated at 200° C. for 1 hour, and heated under reflux at 300° C. for 30 minutes under nitrogen protection. The heating was stopped, and the black mixture liquid resulting from the reaction was allowed to cool to room temperature. The aforementioned synthesis steps for 4 nm $Fe_3O_4$ particles was used to give a dark brown suspension of 8 nm $Fe_3O_4$ particles dispersed in n-hexane. Similarly, 80 mg of 8 nm $Fe_3O_4$ seeds reacted with 2 mmol of ferric triacetylacetonate and 10 mmol of 1,2-dihydroxyhexadecane to produce 10 nm $Fe_3O_4$ nanoparticles. Using this $Fe_3O_4$ seed-mediated growth method, $Fe_3O_4$ nanoparticles with larger size (up to 20 nm) could be synthesized.

2.1.4. Surface Modification of $Fe_3O_4$ Nanoparticle Core

Under atmospheric conditions, 200 µl of n-hexane solvent with 20 mg of dispersed hydrophobic $Fe_3O_4$ nanoparticle core was added to 2 ml of dichloromethane suspension containing 20 mg of tetramethylammonium salt of 11-aminoundecanoic acid. The mixture was shaken for 20 minutes, while a magnet was used to separate the precipitated $Fe_3O_4$ nanoparticles. The solvent and the non-magnetic suspended matter were decanted, the resulting precipitate was washed once with dichloromethane, and then the separation with magnet was performed again to remove excess surfactant. The resulting product was dried under nitrogen gas and then dispersed in deionized water or pH-neutral PBS.

2.2 Hydrothermal Synthesis Method 1.35 g (5 mmol) of ferric chloride hexahydrate ($FeCl_3 \cdot 6H_2O$) was dissolved in 40 mL of ethylene glycol to form a clear solution. To the above solution, 3.6 g of sodium acetate and 1.0 g of polyethylene glycol were added, stirred vigorously for 30 minutes, and then transferred to a 50 ml sealed stainless steel autoclave, reacted at 200° C. for 8-72 hours, and then cooled to room temperature. The black product obtained in the reaction was washed with ethanol for several times and then dried at 60° C. for 6 hours, to obtain a magnetic nanoparticle core having a particle diameter of 10 nm or less.

2.3 Microemulsion Method (Reverse Micellar Method)

5 mmol of $Mn(NO_3)_3$ and 10 mmol of $Fe(NO_3)_3$ were dissolved in 25 mL of deionized water to form a clear and transparent solution; 25 mL of 0.4 M NaDBS ($[CH_3(CH_2)_{11}(C_6H_4)SO_3]Na$) was added to the above iron ion solution, and then added with a large volume of toluene, in which the size of the resulting $MnFe_2O_4$ nanoparticles particles depended on the volume ratio of water and toluene. For example, in order to obtain 8 nm nanoparticles, the volume ratio of water and toluene should be 5:100. After the above mixture liquid was stirred overnight, it became a clear single-phase solution containing reversed micelles.

In order to form colloids in the reversed micelles, 40 mL of 1 M NaOH solution was added dropwise with vigorous stirring, and the stirring was continued for 2 hours. The water and most of the toluene in the solution were removed by distillation to reduce the volume of the solution. The resulting concentrated solution containing suspended colloids was washed with water and ethanol to remove excess surfactant in the solution. A primary magnetic nanoparticle core was obtained by ultracentrifugation, and a nanocrystal was obtained by heating at 350° C. under nitrogen atmosphere for 12 hours.

Example 2: Hydrophobic Polystyrene Surface Modification (Modification on the Magnetic Nanoparticle Core ($MnFe_2O_4$) Obtained in Example 1)

$MnFe_2O_4$ nanoparticles with an average particle size of 9 nm were added to an aqueous solution/3-chloropropionic acid solution with a concentration of 1.0 mol/L initiator, the solution was adjusted to pH of 4 with hydrochloric acid, and stirred overnight. The nanoparticles were collected with a magnet, washed with water for several times to remove excess 3-chloropropionic acid. 0.22 g of dried nanoparticles were added to 8 mL of polystyrene solution under continuous feeding of nitrogen gas, followed by the addition of 4 mL of a xylene solution of 0.3 mmol of CuCl and 1.1 mmol of 4,4'-dinonyl-2,2-dipyridine. The above mixture reacted at 130° C. for 24 h under continuous agitation. The nanoparticles were collected with a magnet and washed repeatedly with toluene to obtain polystyrene-wrapped magnetic iron oxide nanoparticles.

Example 3: Hydrophilic Polyacrylic Acid Modification 1 g of $Fe_3O_4$ obtained in the step 2) and 5 ml of a silane coupling agent (methacryloxypropyltrimethoxysilane, KH570) were mixed with 50 ml of xylene in a reaction flask. Under nitrogen protection, the reaction was carried out under stirring at 80° C. for 3 hours. After the reaction, the mixture was centrifuged and washed with ethanol three times to remove the silane coupling agent adsorbed on the surface of the $Fe_3O_4$, and vacuum-dried for 12 hours. The above-mentioned silane coupling agent-activated $Fe_3O_4$, 40 mg of potassium persulfate and 30 ml of deionized water were added in a flask, reacted under nitrogen protection and stirring at 40° C. for 10 minutes. Then, 4 ml of acrylic acid was slowly dropped into the flask, and reacted under nitrogen protection and stirring at 40° C. for 1 hour. The nanoparticles were magnetically separated, washed three times with deionized water and finally dried under vacuum.

Example 4: Photosensitive Functional Modification of Nanoparticles

1. Synthesis of Photosensitive Functional Monomer

The synthesis method of photosensitive monomer with photo-crosslinking characteristics comprised: 4-vinylbenzophenone (4VBP) and styrene monomer were directly polymerized by atom transfer radical polymerization (ATRP) to obtain a photosensitive polystyrene-polyvinylbenzophenone copolymer (PS-PVBP), wherein the specific steps were as follows: in a dry Schlenk tube connected with a reflux condenser, Cu(I)Br (0.695 mg, 4.8 umol), 4VBP (1.0 g, 4.8 mmol), styrene (2 u, 20 umol) and 4-vinylbenzophenone (1 µL, 4.8 umol) were added, and the mixture was degassed for three times by means of freeze-pump-thaw circulation. Methyl bromopropionate (5.35 µL, 48 umol) was added to the above mixture at −78° C. under condition of nitrogen with positive pressure, and the mixture was degassed again for three more times by means of freeze-pump-thaw circulation. Polymerization was carried out by heating the mixture to a temperature of 85° C. under negative pressure, and the reaction was allowed to proceed for 4 hours. The above Schlenk tube was immersed in liquid nitrogen, and 10 ml of dichloromethane was added to dissolve the polymer. The resulting solution was precipitated twice with methanol (2×300 mL) to give $PS_x$-$PVBP_y$ as a light yellow solid, wherein x:y~(60%-90%), and a preferred composition was $PS_{75}$-$PVBP_{25}$. In the same way, $PS_{75}$-$PVBP_{25}$-$PAA_{100}$ could be obtained by adding hydrophilic monomer acrylic acid.

2. Preparation of Nanoparticles Wrapped with Photosensitive Cross-Linked Micelles (Polystyrene$_{75}$-co-polyvinylbenzophenone$_{25}$)-polyacrylic acid$_{100}$, namely $(PS_{75}$-co-$PVBP_{25})_{115}$-b-$PAA_{100}$, was chosen as a polymer to form micelles in aqueous solution. 5 mg of $(PS_{75}$-co-$PVBP_{25})_{115}$-b-$PAA_{100}$ and 10 mg of $Fe_3O_4$ obtained in step 2) were dissolved in 10 ml of dimethylformamide (DMF) solution; and then double distilled water (0.1 ml/min) was gradually added under vigorous stirring. When the volume of water reached 60%, the resulting solution was added to a dialysis membrane with a molecular weight cut off of 12K-14K and dialyzed against water for 24 hour to remove DMF, and then the micellar solution was transferred to a quartz tube and irradiated with a laser at different time periods (emission wavelength: 315-400 nm) to form a photosensitive monomer-wrapped nanoparticle.

Example 5: Thermosensitive Functional Modification of Nanoparticles 1 g of $Fe_3O_4$ obtained in step 2) of Example 1 and 5 ml of a silane coupling agent (methacryloxypropyltrimethoxysilane, KH570) were mixed with 50 ml of xylene in a reaction flask. Under nitrogen protection, the reaction was carried out with stirring at 80° C. for 3 hours. After the completion of the reaction, the mixture was centrifuged and washed with ethanol three times to remove the silane coupling agent adsorbed on the surface of the $Fe_3O_4$, and vacuum-dried for 12 hours. The above-mentioned silane coupling agent-activated $Fe_3O_4$, 40 mg of potassium persulfate and 30 ml of deionized water were added in a flask, reacted under nitrogen protection and stirring at 40° C. for 10 minutes. Then, 4 ml of N-isopropylacrylamide aqueous solution was slowly dropped into the flask, and reacted under nitrogen protection and stirring at 40° C. for 1 hour. The nanoparticles were magnetically separated, washed three times with deionized water and finally dried in vacuo.

Example 6: pH-Sensitive Functional Modifications of Nanoparticles 1 g of $Fe_3O_4$ obtained in step 2) of Example 1 and 5 ml of a silane coupling agent (methacryloxypropyltrimethoxysilane, KH570) were mixed with 50 ml of xylene in a reaction flask, and reacted under nitrogen protection and stirring at 80° C. for 3 hours. After the completion of the reaction, the mixture was centrifuged and washed with ethanol three times to remove the silane coupling agent adsorbed on the surface of the $Fe_3O_4$, and dried in vacuo for 12 hours. The above-mentioned silane coupling agent-activated $Fe_3O_4$, 40 mg of potassium persulfate and 30 ml of deionized water were added in a flask, reacted under nitrogen protection and stirring at 40° C. for 10 minutes. Then, 4 ml of dimethylaminoethyl methacrylate aqueous solution was slowly dropped into the flask, and reacted at 40° C. for 1 hour under stirring and nitrogen protection. The nanoparticles were magnetically separated, washed three times with deionized water and finally dried in vacuo.

Example 7: Biocompatibility Evaluation

Cell Plating: 293t cells in logarithmic growth phase were digested, counted after centrifugation, and plated on a 96-well plate with a cell density of $5.0 \times 10^4$/well. 100 µl of serum-containing medium was added to each well. The surrounding blank wells were each complemented with 100 µl of serum-containing medium. The plate was placed in a 7% $CO_2$, 37° C. cell incubator overnight. The hydrophilically modified magnetic nanoparticles in an amount of 100 µl per well were added to the cell wells and incubated with N87 cells, wherein the magnetic nanoparticles obtained in Example 3 was used in concentrations of 0.1, 0.2, 0.4, 0.8, 1.0 mg/ml respectively. After incubated at 37° C. for 24 hours, the cells were gently washed twice with culture medium, and then the cell viability was measured with a Cell Counting Kit-8 kit, in which the detection conditions were as follows: 10 µl of CCK-8 reagent per well, incubate at 37° C. for 2 hours, read the absorbance value at 450 nm with BIO-TEK EL×800 automatic microplate reader, and calculate the cell viability. The results shown in FIG. 5, indicating the synthesized hydrophilically modified magnetic nanoparticles had good biocompatibility and almost no toxicity in vivo, and giving preliminary evidences of applicability for in vivo experiments.

Figure 5:
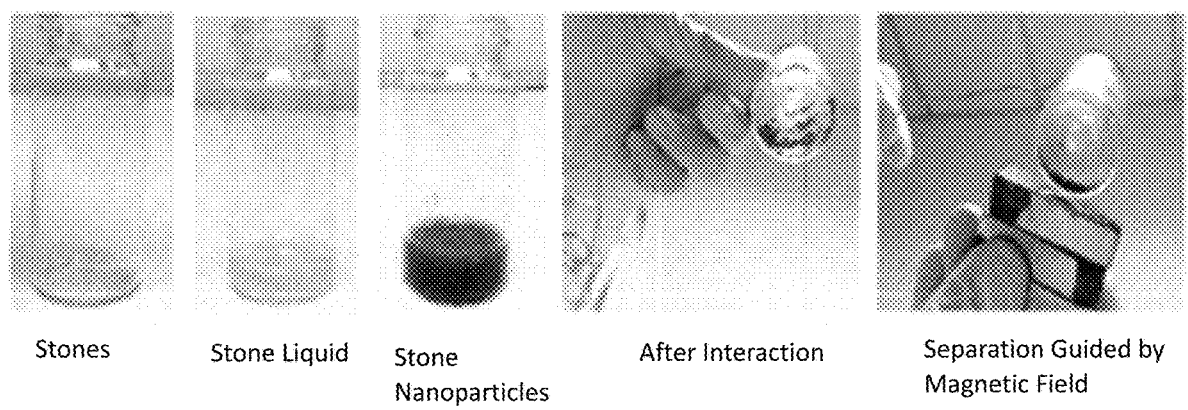
FIG. 5 shows a graph of stone separation with in vitro assistance for the nanoparticles obtained in Example 6 of the present invention.

Example 8: Evaluation of In Vitro Stone Separation with Assistance of Nanoparticles As shown in FIG. 5, a certain amount of stones were weighed, pulverized with a pestle into a powder (particle size 0.5-2 mm), poured into a transparent glass bottle, and PBS solution was added to obtain a stone liquid. After being mixed uniformly, the hydrophilically modified magnetic particles at a concentration of 1 mg/ml was used as a separation liquid and added, and then gently shaken. After standing for 5 minutes, separation was carried out with a magnet. During standing, it was observed that the color of the mixture gradually faded, and after 5 minutes, it was observed that the black magnetic particles were adsorbed on the surface of the stone. Under the guidance of the magnetic field, the stones with magnetic particles adsorbed on their surface moved toward the magnet.

Example 9: Evaluation of In Vivo Safety of Nanoparticles in Animals

Figure 6:
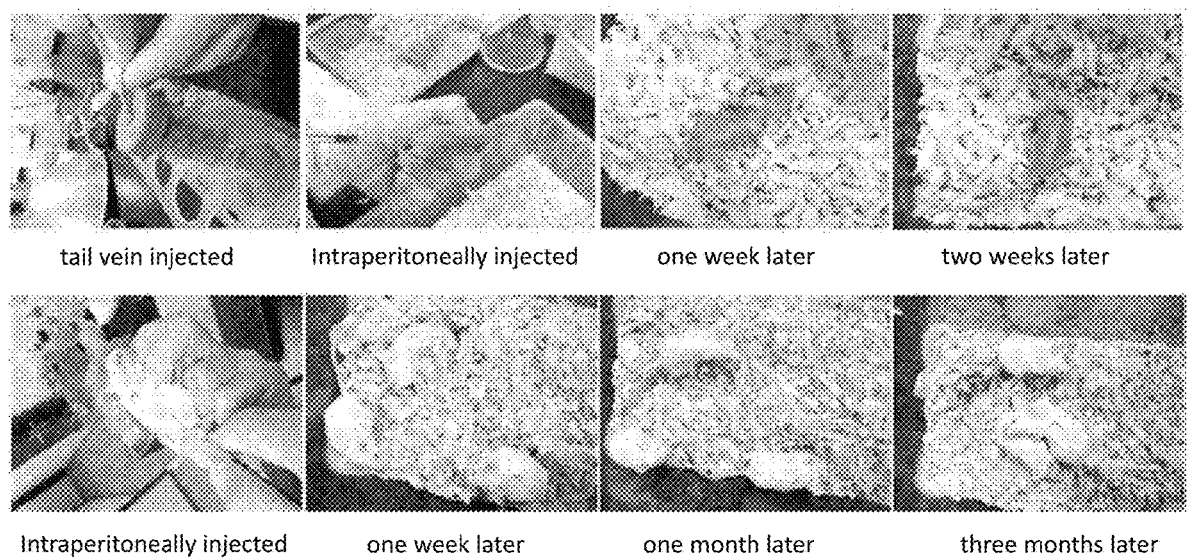
FIG. 6 shows a graph of safety evaluation in body of animals for the nanoparticles of the present invention.
Figure 7:
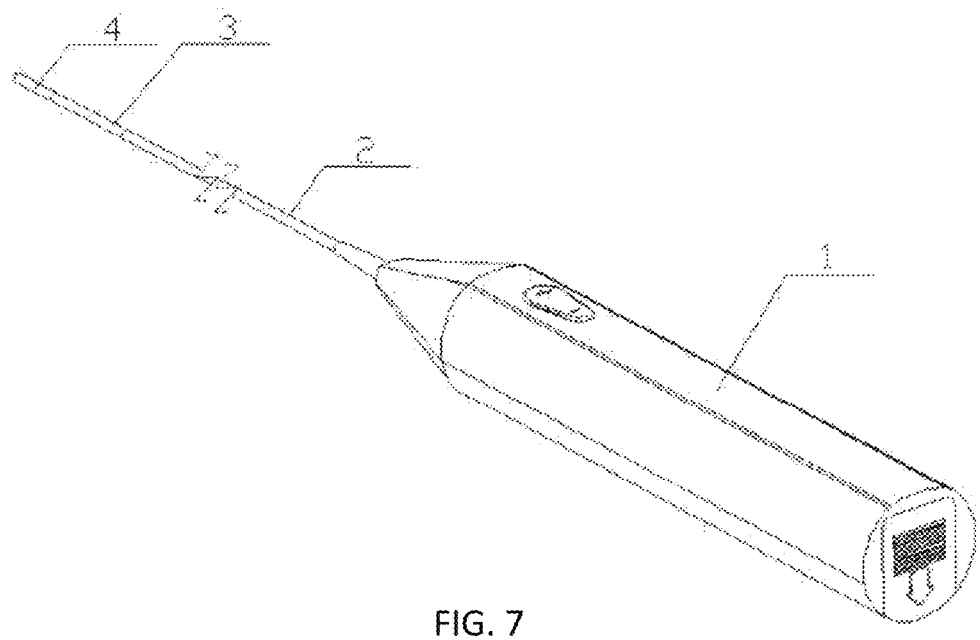
FIG. 7 shows an overall schematic diagram of the magnetic target separation instrument in the present invention.
Figure 8:
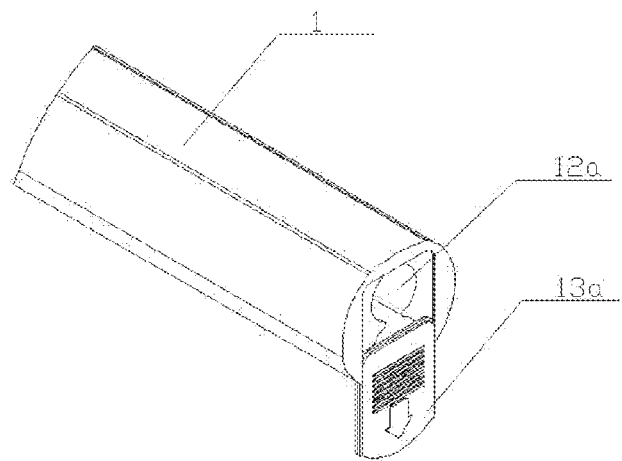
FIG. 8 shows a schematic view of the handle portion of the magnetic target separation instrument in the present invention.
Figure 9:
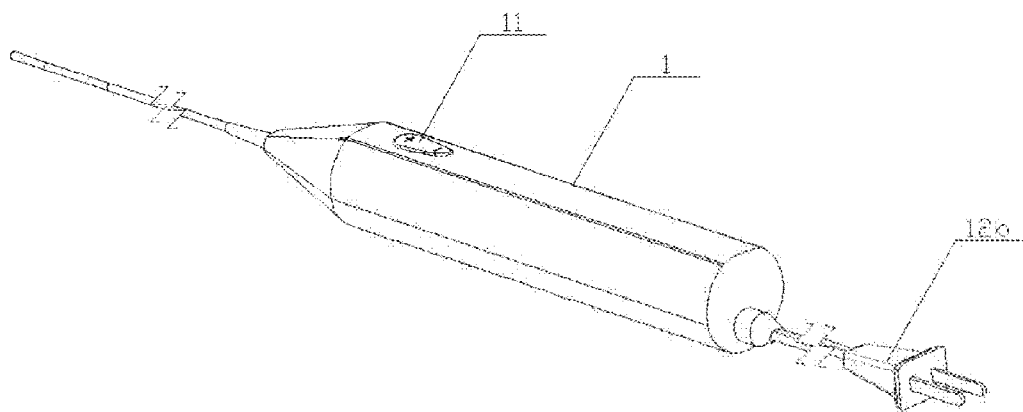
FIG. 9 shows a schematic view of the magnetic target separation instrument with an AC power supply according to the present invention.
Figure 10:
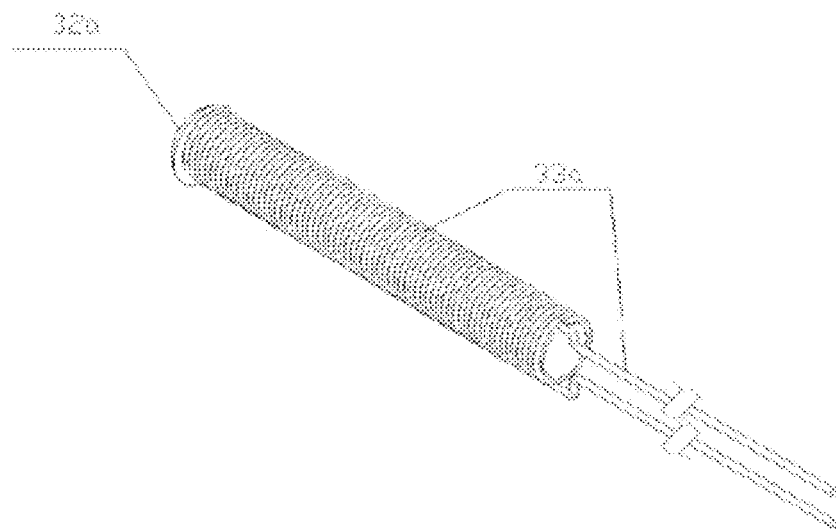
FIG. 10 shows a schematic view of the internal structure of the magnetic target separation instrument using an electromagnet as magnetic field source according to the present invention.
Figure 11:
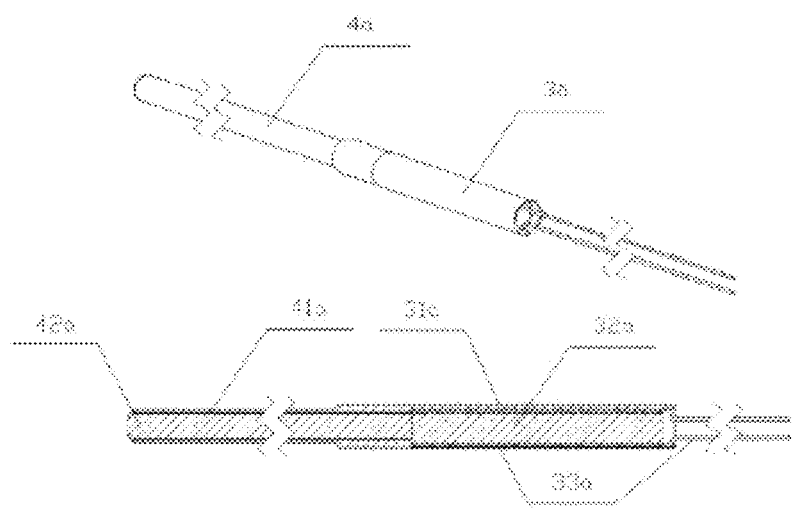
FIG. 11 shows a schematic view of the magnetic target separation instrument of the present invention which uses an electromagnet as magnetic field source and a magnetically permeable material section at distal end.

As shown in FIG. 6, one 6-week-old nude rat and 3 mice were intraperitoneally injected and tail vein injected, respectively. The hydrophilically modified magnetic nanoparticles at a concentration of 0.5 mg/ml and in an amount of 200 µL were used for the injection for consecutive two days. The living conditions of the mice were observed periodically (such as one week, two weeks, etc.). The results showed that after intravenous injection of 200 µL of magnetic nanoparticle solution, no obvious toxicity was found in the nude rat and the mice within 1 week; and after intraperitoneal injection of particle solution at the same concentration 3 times, it was found that the rat and the mice had good survival status. This shows that the prepared magnetic nanoparticles have good biocompatibility, and such preliminary assessment shows they basically have no acute toxicity and chronic toxicity.

Example 10: Using Magnetic Nanoparticles in Removal of Urinary Stones

In the treatment of disease of kidney stones, an ureteroscope was used for holmium laser lithotripsy. In the operation, after crushing process of kidney stones with holmium laser, 200 ml of the hydrophilic magnetic nanoparticle solution of Example 3 according to the present invention was injected into the kidney through the working channel of the ureteroscope, so that the hydrophilic magnetic nanoparticle solution was thoroughly mixed with the stone debris. After about 3 minutes, the nanoparticles in the solution completely adhered to the surface of the stone debris, and magnetized the stone debris. The above-mentioned magnetic target separation instrument for removal of stones in urinary system, in which a NdFeB permanent magnet was used as the magnetic field source 3, was inserted into the kidney through the working channel of the ureteroscope. Under the action of the magnetic field at the distal end of the magnetic target separation instrument, the magnetized stone debris moved closer to the distal end of the magnetic target separation instrument and attracted to the magnetic target separation instrument. Finally, the magnetic target separation instrument filled with stones debris at its distal end together with the ureteroscope were drawn from the body through the soft sheath of the ureteroscope. After the stone debris were removed from the distal end of the magnetic target separation instrument, the magnetic target separation instrument could re-enter into the endoscope to perform stone removal operation, until all of the stone debris inside the kidney were removed from the body. In this Example, the stone had a diameter of about 20 mm and was located in the lower kidney calyx. By using the magnetic target separation instrument in combination with the hydrophilic magnetic nanoparticle material of the present invention, all (100%) of the stone debris were removed from the body. In comparison with the traditional method of removing stones by baskets and the method of pulverizing stones and then allowing patients to discharge stone debris, the technical solutions of the present invention achieved simple, efficient and complete removal of stones, thereby greatly improving the efficiency and safety of stone removal operations.

Example 11

Figure 15:
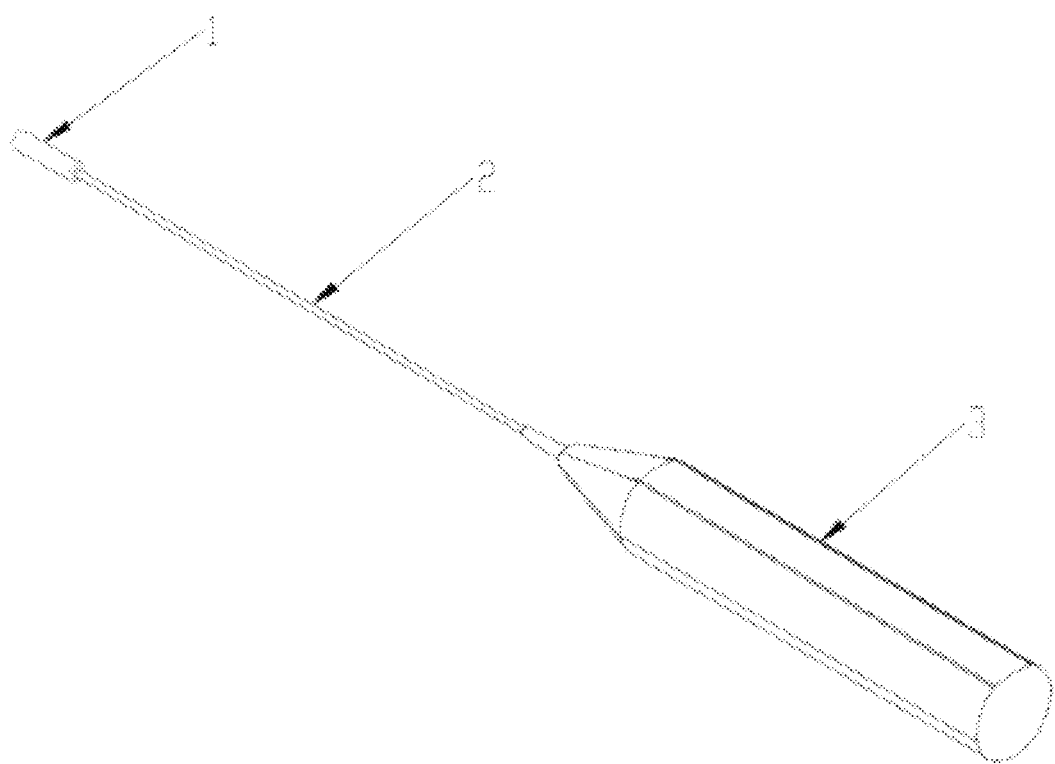
FIG. 15 shows an overall schematic view of an exemplary magnetic target separation instrument of the present invention.
Figure 16A:
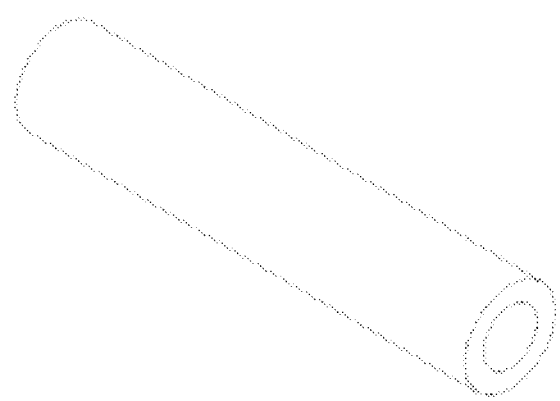
FIG. 16A shows a schematic view of one connecting rod material.
Figure 16B:
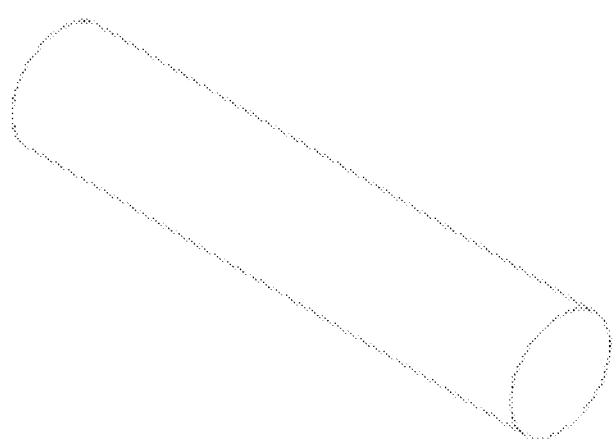
FIG. 16B shows a schematic view of another connecting rod material.
Figure 16C:
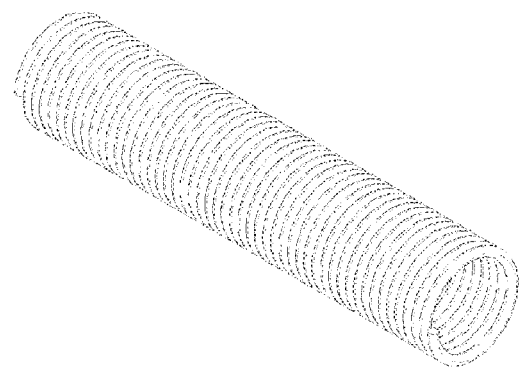
FIG. 16C shows a schematic view of yet another connecting rod material.
Figure 16D:
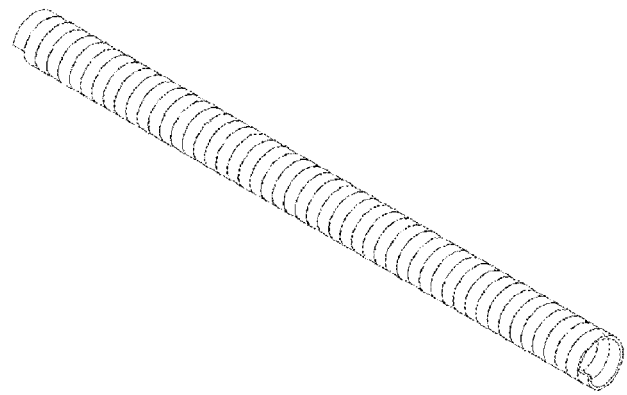
FIG. 16D shows a schematic view of yet another connecting rod material.
Figure 16E:
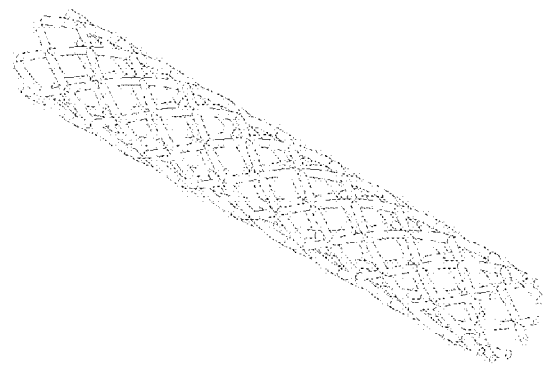
FIG. 16E shows a schematic view of yet another connecting rod material.

The present Example provided a magnetic target separation instrument which was composed of a magnetic end 1, a connecting rod 2 and a handle 3 (FIG. 15). The connecting rod 2 was connected at its distal end with the magnetic end 1, and connected at its proximal end with the handle 3. The connecting rod 2 was made of a material with a certain flexibility, for example, the structure of the connecting rod 2 could be a tube 2a (FIG. 16A), a wire 2b (FIG. 16B), a spring tube 2c (FIG. 16C), a hypotube 2d (FIG. 16D), a braided tube 2e (FIG. 16E), as well as combinations formed by splicing or nesting the above structures or forms. The connecting rod 2 had a diameter between 0.5 mm and 5 mm. Depending on the method of use, one skilled in the art could choose different diameters for the connecting rod. For example, when the magnetic target separation instrument according to the present invention was introduced into the human body through an endoscope working channel, the diameter of the connecting rod 2 was preferably 0.5 mm to 1.2 mm. Alternatively, when the magnetic target separation instrument according to the present invention was introduced into the human body through the ureteral sheath, the diameter of the connecting rod 2 was preferably 1 mm to 4.5 mm. When the diameter of the connecting rod 2 was greater than 1 mm, the connecting rod 2 may be a hollow structure, through which a metal wire, a cable, a cord, a catheter, an optical fiber, and any combination of the above can pass, respectively.

Example 12

Figure 17:
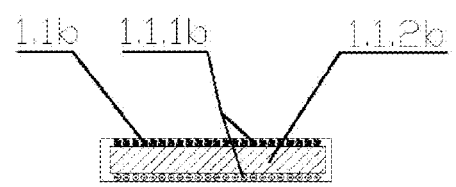
FIG. 17 shows a schematic view of one magnetic end.
Figure 17:
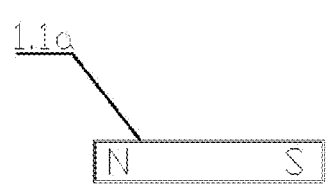
Figure 17:
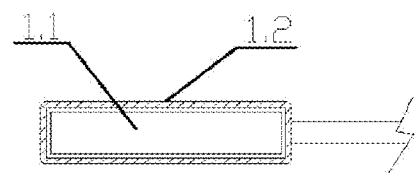
Figure 18:
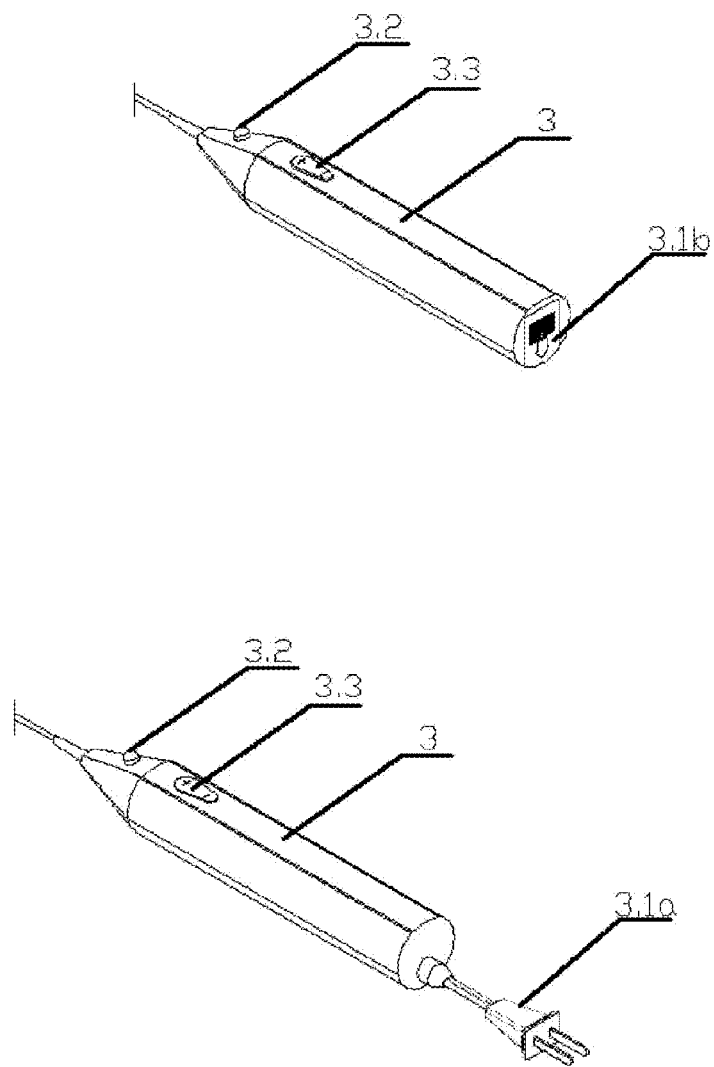
FIG. 18 shows a schematic view of the handle of a magnetic target separation instrument in which the magnet end is an electromagnet.

The present example provided a magnetic target separation instrument, which comprised a magnetic end 1, the magnetic end 1 was a magnetic component 1.1, and a permanent magnet made of a magnetic material could be used as the magnetic component 1.1a, the magnetic material included, but was not limited to, an alloy magnetic material, a ferrite magnetic material and an intermetallic compound magnetic material, such as: aluminium-nickel-cobalt, iron-chromium-cobalt, iron-cobalt-vanadium, barium ferrite, strontium ferrite, neodymium-iron-boron, samarium-cobalt, manganese-bismuth and other materials. The handle 3 was connected to the magnetic end 1 through the connecting rod 2, wherein the handle 3 was used for controlling the magnetic end 1 to enter or leave the endoscope channel (FIG. 17).

Example 13

The present example provided a magnetic target separation instrument, which comprised a magnetic end 1, the magnetic end 1 was a magnetic component 1.1, an electromagnet could be used to make the magnetic component 1.1b, and the electromagnet was made of a cable-wound coil 1.1.1b. Further, as the inner core 1.1.2b, a magnetically permeable material for enhancing magnetic field strength could be added to the cable-wound coil, and the magnetically permeable material includes, but is not limited to, pure iron, ferrite soft magnetic material, iron-nickel alloy, ferro-silicon alloy, vanadium-iron-vanadium alloy, nano-crystalline soft magnetic materials, amorphous soft magnetic materials. The handle 3 was connected to the magnetic end 1 through the connecting rod 2, wherein the handle 3 was characterized in that the handle was provided with an AC plug 3.1a or a DC battery chamber 3.1b for supplying power to the electromagnet. Further, the handle was provided with a power switch 3.2 for controlling whether the electromagnet was electrified or not. Further, the handle was provided with a regulating switch 3.3 for adjusting the magnitude of the current so as to adjust the magnetic field strength of the electromagnet.

Example 14

Figure 19:
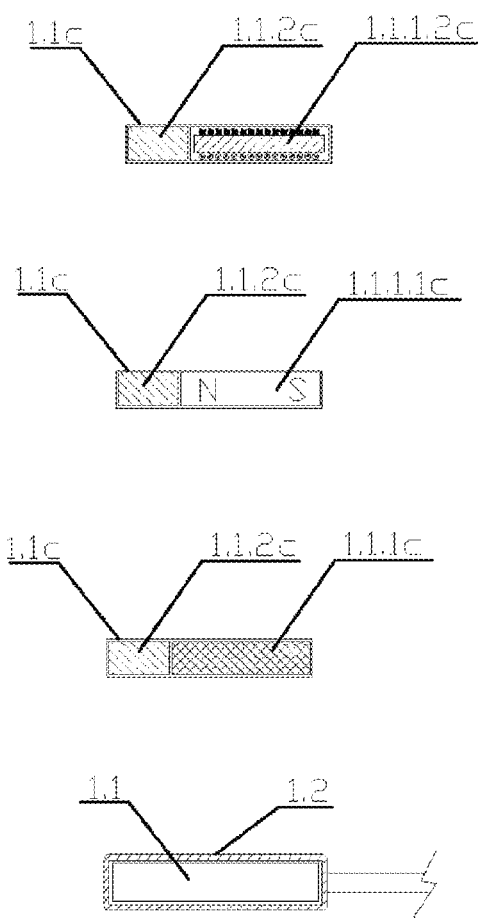
FIG. 19 shows a schematic view of another magnetic end.

The present example provided a magnetic target separation instrument, which comprised a magnetic end 1, the magnetic end 1 was a magnetic component 1.1, a magnetic field source 1.1.1c and a high-efficiency magnetically permeable end 1.1.2c could form the magnetic component 1.1c. The magnetic field source 1.1.1c could be a permanent magnetic field source 1.1.1.1c made of a permanent magnet or an electromagnetic field source 1.1.1.2c made of an electromagnet. The high-efficiency magnetically permeable end 1.1.2c is joined to the distal end of the magnetic field source 1.1.1c and was used to guide, extend, derive, disperse and cross-link the magnetic field produced by the magnetic field source with no loss or low loss, so as to compensate the simplicity in terms of surface area, volume, shape, flexibility and strength of the magnetic end 1 which were caused by the relatively simple type of the magnetic field source 1.1.1c, to better adapt to the human blood vessels, urinary system and other anatomical structures, and to ultimately realize the separation of magnetic targets under a complex and volatile environment. The material of the high-efficiency magnetically permeable end 1.1.2c included, but was not limited to, pure iron, low carbon steel, ferrosilicon alloy, ferroaluminum alloy, sendust, ferronickel alloy, iron-cobalt alloy, soft ferrite, amorphous soft magnetic alloy, ultra-crystalline soft magnetic alloy and other materials. The handle 3 was connected to the magnetic end 1 through the connecting rod 2, wherein the handle 3 was used for controlling the magnetic end 1 to enter or leave the endoscope channel (FIG. 19).

Example 15

Figure 20:
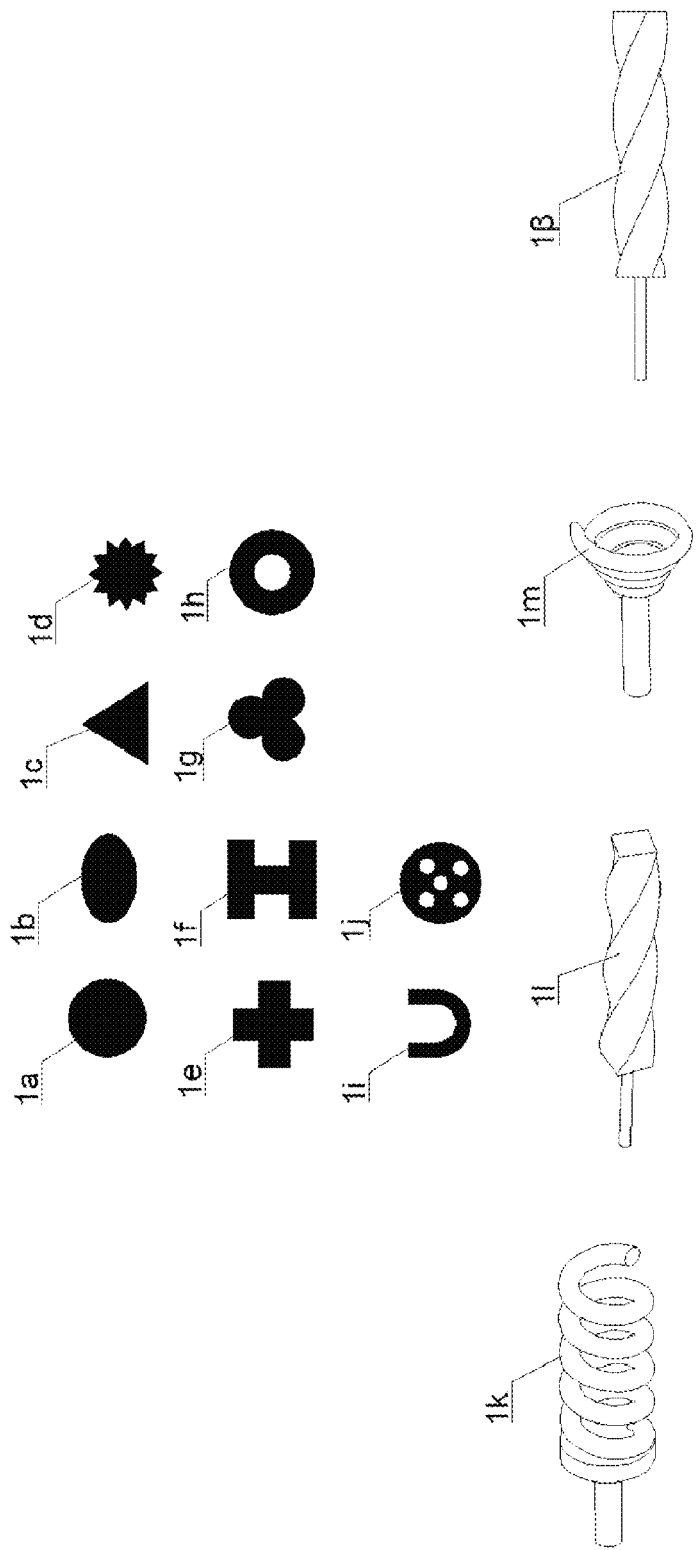
FIG. 20 shows a schematic view of the cross-sectional shape of the columnar magnetic end.
Figure 21:
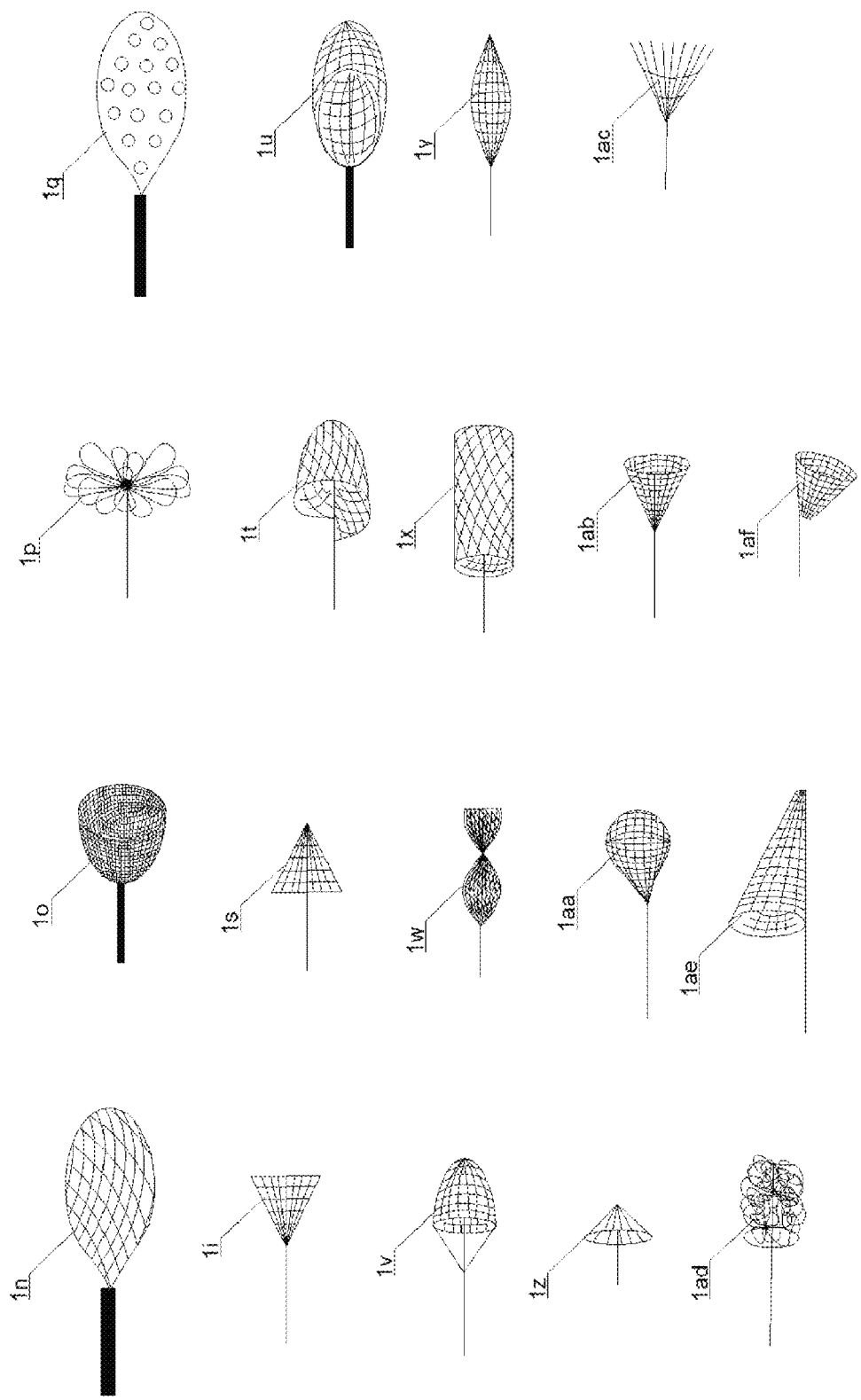
FIG. 21 shows a schematic view of the mesh shape of the reticulated magnetic end.

The present example provided a magnetic target separation instrument, which comprised a magnetic end 1, the shape of the magnetic end 1 could be made into a column shape. Still further, the cross-sectional shape of the magnetic end in column shape included, but was not limited to, round shape 1a, oval shape 1b, polygon shape 1c, radial shape 1d, cross shape 1e, I-shape 1f, petal shape 1g, annular shape 1h, U-shape 1i, porous shape 1j, spiral shape 1k, torsion shape 1l, coiled shape 1m, twisted shape 1β and other shapes (FIG. 20). The shape of the magnetic end 1 could be made into a reticulum shape. Further, the reticulated magnetic end could be woven from a single- or multi-stranded magnetic or magnetically permeable materials, and its shape could be woven reticulum shape 1n, coiled reticulum shape 1o, knotted rope reticulum shape 1p, hollow mesh 1q, radial reticulum shape 1r, convergent reticulum shape 1s, cross-section asymmetric reticulum shape 1t, open reticulum shape 1u, pocket-type reticulum shape 1v, spiral-type reticulum shape 1w, barrel-shaped reticulum shape 1x, spindle-shaped reticulum shape 1y, umbrella-shaped reticulum shape 1z, drop-shaped reticulum shape 1aa, funnel-shaped reticulum shape 1ab, broom-shaped reticulum shape 1ac, disorderly entangled reticulum shape 1ad, axial-side convergent reticulum shape 1ae, axial-side divergent reticulum shape 1af (FIG. 21). Furthermore, the surface of the columnar magnetic end or the reticulated magnetic end could be coated with overcoat layer 1.2 (FIG. 17 or FIG. 19), and the overcoat layer could be of a biocompatible material such as Teflon, parylene, polyurethane, thermoplastic polyurethane. Still further, the overcoat layer 1.2 on the surface of the columnar magnetic end or the reticulated magnetic end could be of a magnetic material or a material having a high magnetic permeability ($\mu$>1). The handle 3 was connected to the magnetic end 1 through the connecting rod 2, wherein the handle 3 was used for controlling the magnetic end 1 to enter or leave the endoscope channel.

Example 16

Figure 22:
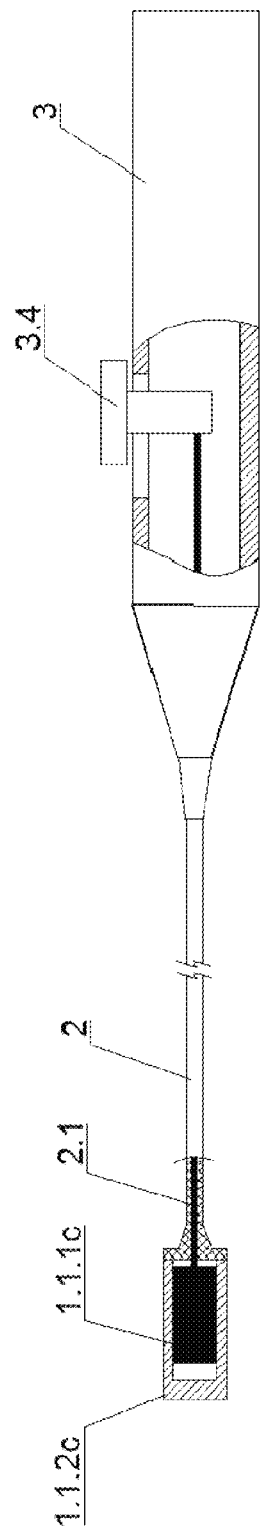
FIG. 22 shows a schematic view of the cross-sectional shape of yet another exemplary magnetic target separation instrument of the present invention.

The present example provided a magnetic target separation instrument, which comprised a magnetic end 1, the magnetic end 1 was magnetic component, and the magnetic component could be composed of a magnetic field source 1.1.1e and a high-efficiency magnetically permeable end 1.1.2c. Further, in the magnetic component, the magnetic field source 1.1.1c is joined to the high-efficiency magnetically permeable end 1.1.2c axially along the axis of the connecting rod 2, or the magnetic field source is coated by the high-efficiency magnetically permeable end. Further, here exists a relative movement between the magnetic field source 1.1.1c and the high-efficiency magnetically permeable end 1.1.2c. In that case, an axial rigid push-rod 2.1 was connected to the magnetic field source 1.1.1c, the rigid push-rod 2.1 passed through the lumen of the connecting rod 2 and the other end was fixed on a control push-rod 3.4 of the handle 3, the relative distance between the magnetic field source 1.1.1c and the high-efficiency magnetically permeable end 1.1.2c could be changed by pushing the control push-rod 3.4 so as to adjust the magnetic field intensity in the high-efficiency magnetically permeable end. After the magnetic target separation instrument provided by the invention collected, adsorbed and removed a magnetic target, this function could fulfill the quick removal of the magnetic targets from the instrument so as to prepare the instrument for re-entering the human body. The handle 3 was connected to the magnetic end 1 through the connecting rod 2, wherein the handle 1 was used for controlling the magnetic end 1 to enter or leave the endoscope channel. Further, the handle 3 was provided with a control push-rod 3.4, the control push-rod 3.4 was connected to the magnetic field source 1.1.1e in the magnetic end through an axial rigid rod 2.1. Further, the axial rigid rod 2.1 passed through the lumen of the connecting rod 2 and is slidingly disposed in the connecting rod 2; the relative distance between the magnetic field source 1.1.1c and the high-efficiency magnetically permeable end 1.1.2c could be changed by pushing and pulling the control push-rod 3.4 so as to change the adsorption strength of the magnetic end to the magnetic target, to make it possible to quickly separate the magnetic targets from the surface of the magnetic end in vitro, thereby facilitating the re-entry of the instrument into the human body to collect, adsorb and remove the magnetic targets (FIG. 22).

Example 17

Figure 23A:
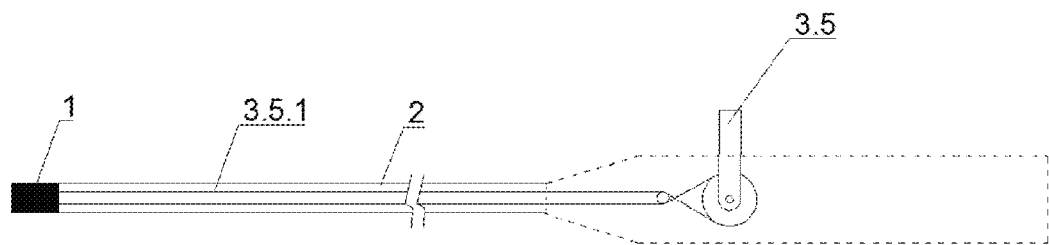
FIG. 23A and FIG. 23B show schematic views of the cross-sectional shape of still another exemplary magnetic target separation instrument of the present invention.
Figure 23B:
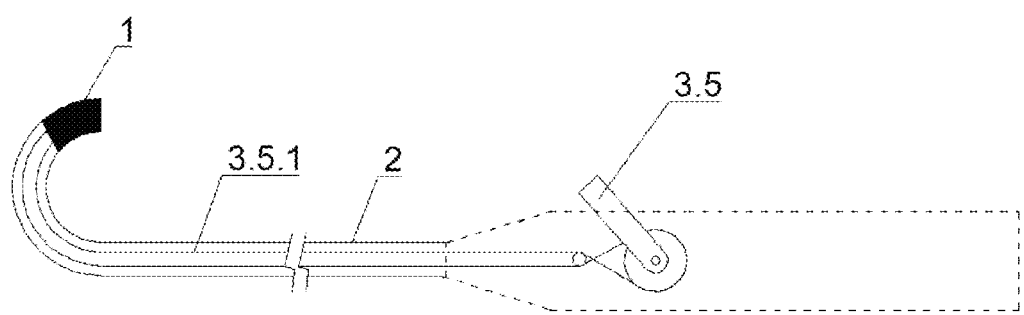

The present example provided a magnetic target separation instrument, which comprised a magnetic end 1, the magnetic end 1 contained a steel wire or cord 3.5.1 for driving the bending of the magnetic end. Further, there are one or two or more pieces of the steel wire or cord 3.5.1. One end of the steel wire or cord 3.5.1 was fixed in the magnetic end 1, passed through the connecting rod 2, and the other end was fixed on an angle adjustment shaft 3.5 of the handle, so that by manipulating the angle adjustment shaft 3.5, the magnetic end 1 could be controlled to bend at an angle away from the axial direction of the connecting rod 2. The handle 3 was connected to the magnetic end 1 through the connecting rod 2, wherein the handle 3 was used for controlling the magnetic end to enter or leave the endoscope channel. Further, the handle was provided with an angle adjustment shaft 3.5, the angle adjustment shaft 3.5 pulled the magnetic end 1 via one or two or more pieces of steel wire or cord 3.5.1 passing through the connecting rod 2, so that the magnetic end 1 could bend at an angle away from the axial direction of the connecting rod 2 to adapt to the purpose for separating the magnetic targets from different body cavities under complicated environments (FIG. 23A and FIG. 23B).

Example 18

Figure 24:
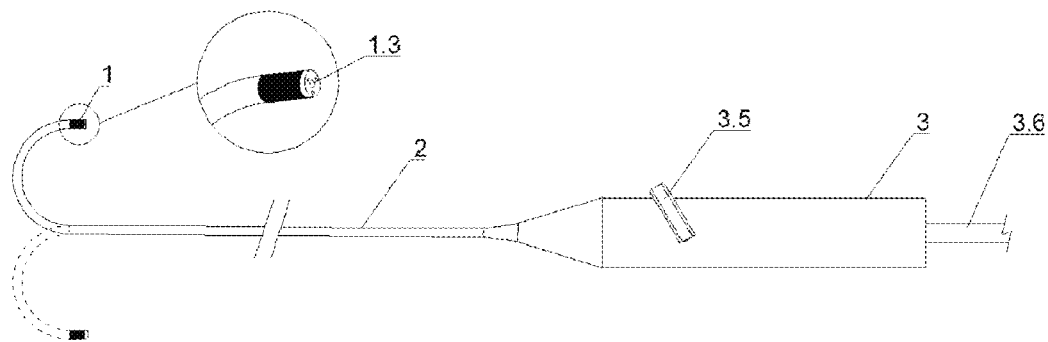
FIG. 24 shows overall and partial schematic views of a magnetic target separation instrument integrated with an image acquisition module.

The present example provided a magnetic target separation instrument, which comprised a magnetic end 1, the magnetic end 1 was integrated with an image acquisition module 1.3. Further, the image acquisition module 1.3 a lens and a CCD, or comprises a lens and a CMOS, or comprises a lens and an image transmission fiber, or comprises only an image transmission fiber. Preferably, the image acquisition module 1.3 was composed of a lens and a CMOS. Further, the magnetic end 1 with the image acquisition module 1.3 included a steel wire or cord 3.5.1 for driving the magnetic end to bend, wherein the steel wire or cord 3.5.1 was fixed in the magnetic end 1 at one end of the steel wire or cord, passed through the interior of the connecting rod 2, and was fixed on the angle adjustment shaft 3.5 of the handle at the other end of the steel wire or cord; by manipulating the angle adjustment shaft 3.5, the magnetic end 1 could be controlled to bend at an angle away from the axial direction of the connecting rod 2. The handle 3 was connected to the magnetic end 1 through the connecting rod 2, wherein the handle 3 was used for controlling the magnetic end to enter or leave the endoscope channel. Further, the handle 3 was provided with an angle adjustment shaft 3.5, the angle adjustment shaft 3.5 pulled the magnetic end 1 through one or two or more pieces of a steel wire or cord 3.5.1 passing through the connection rod, so that the magnetic end 1 could bend at an angle away from the axial direction of the connecting rod 2 to adapt to the purpose of separating the magnetic targets in different body cavities under complicated environments. Further, the handle 3 was provided with a video image signal transmission interface 3.6 to connect an external video display device so as to facilitate monitoring the surgical field and process recording (FIG. 24). The external video display device belonged to the prior art and was not included in the present example, and thus its details were not described herein.

Example 19

Figure 25:
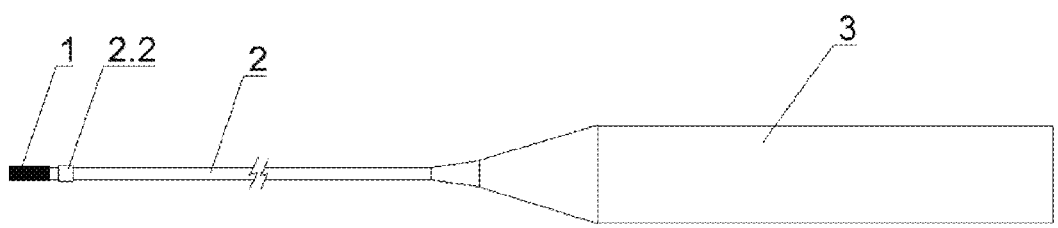
FIG. 25 shows an overall schematic view of a magnetic target separation instrument with a connection mechanism.
Figure 26:
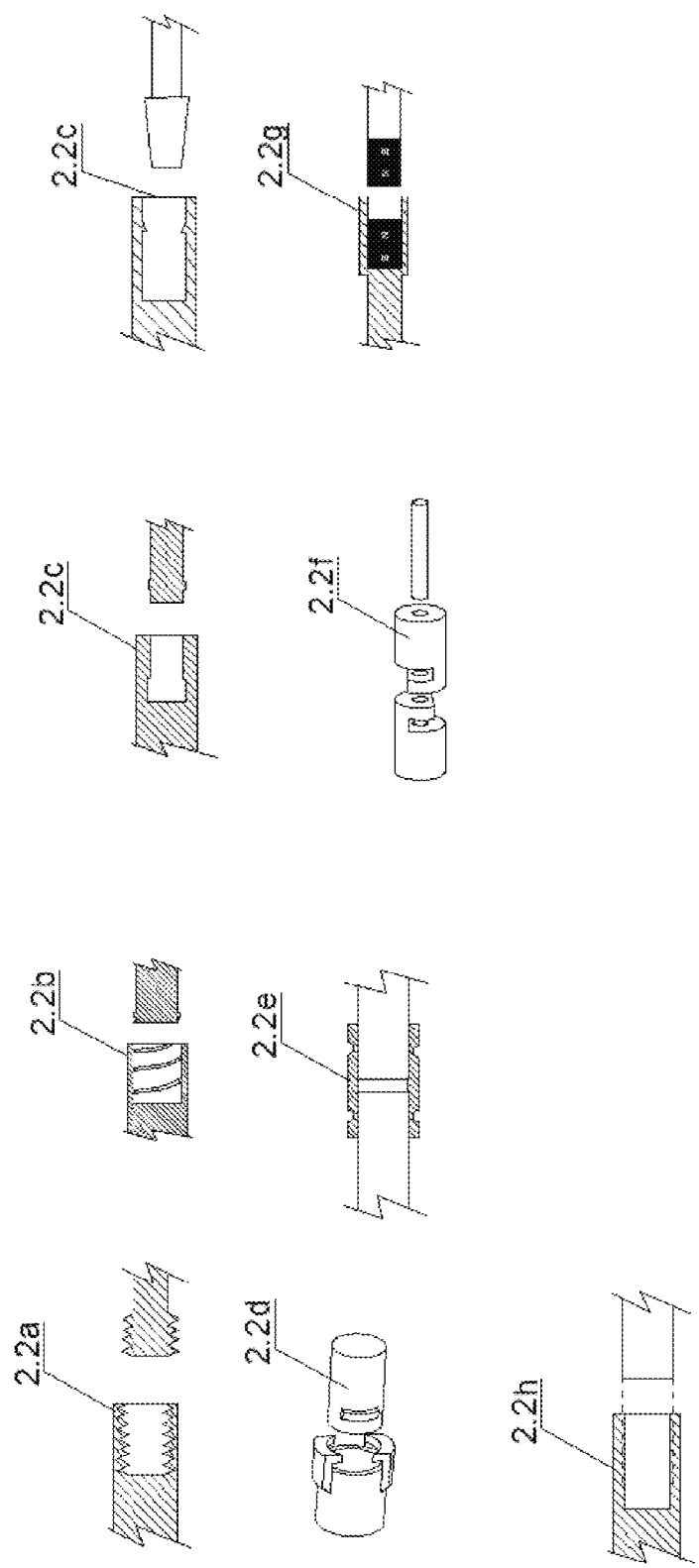
FIG. 26 shows a schematic view of a quick connect mechanism.

The present example provided a magnetic target separation instrument, which comprised a magnetic end 1 and a connecting rod 2, the connection relationship between the magnetic end 1 and the connecting rod 2 was that the magnetic end 1 was spliced with the distal end of the connecting rod 2, or the connecting rod passed through the magnetic end 2, or the connecting rod 2 and the magnetic end 1 were connected by bonding, or the connecting rod 2 and the magnetic end 1 were connected by covering with the same material, or the connecting rod 2 and the magnetic end 1 were connected by metal crimping, or the connecting rod 2 and the magnetic end 1 were connected by a quick connecting mechanism 2.2 (FIG. 25), the quick connecting mechanism included, but was not limited to, a screw thread 2.2a, a Luer taper 2.2b, a snap joint 2.2c, a screw buckle 2.2d, a socket component 2.2e, a plug-in component 2.2f, a magnetic component 2.2g, an interference fit component 2.2h and so on that could achieve quick connection (FIG. 26).

Example 20

The present example provided a method for using the magnetic target separation instrument according to the present invention, comprising: 1) firstly, the stones in the body were crushed by means of a traditional lithotripsy such as those described in the Background Art; 2) a functional material with magnetic properties was injected into the region containing the crushed stones through the endoscope working channel; 3) the functional material with magnetic properties had a physical or chemical interaction on the surface of the stones and wrapped the surface of the stones so as to finally magnetize the stones; 4) the magnetic target separation instrument of the present invention was introduced to gather the magnetized stones together in the front end of the instrument by the magnetic field of the magnetic end, and finally the gathered stones and the instrument together were removed from the body to fulfill the purpose of gathering stones in non-contact mode and bulk removal of stones at a high efficiency.

While many embodiments of the invention have been shown and/or discussed herein, it is not intended that the invention is limited thereto. It is anticipated that the scope of the present invention will be the same as what is allowed in the art, and equally appreciated according to the description. Therefore, the above description should not be construed as limiting, but merely as exemplifications of specific embodiments. Those skilled in the art can envision other variations within the scope and spirit of the claims appended hereto.

The invention claimed is:

1. A magnetic target separation instrument, comprising:
   a magnetic end,
   a connecting rod, and
   a handle;
   wherein a distal end of the connecting rod is connected to the magnetic end, a proximal end of the connecting rod is connected to the handle;
   wherein the connecting rod is made of a flexible material;
   wherein the magnetic end is a magnetic component;
   wherein the magnetic component is composed of a magnetic field source and a high-efficiency magnetically permeable end;
   wherein the high-efficiency magnetically permeable end splices a distal end of the magnetic field source;
   wherein the magnetic field source of the connecting rod is joined to the high-efficiency magnetically permeable end axially along the axis of the connecting rod, or the magnetic field source is coated by the high-efficiency magnetically permeable end,
   wherein the instrument has a relative movement between the magnetic field source and the high-efficiency magnetically permeable end;
   wherein the handle comprises a control push-rod which is connected to the magnetic field source within the magnetic end through an axial rigid rod or rigid tube; and
   wherein the axial rigid rod or rigid tube passes through a lumen of the connecting rod and is slidingly disposed in the connecting rod.

2. The magnetic target separation instrument according to claim 1,
   wherein the connecting rod has a structure selected from a tube, and a wire; and
   wherein the tube is selected from a spring tube, a hypotube and a braid tube; or
   wherein the connecting rod is formed by splicing or nesting the structures selected from a tube, and a wire; or
   wherein a raw material of the connecting rod is selected from the group consisting of a polymer material and a metal material.

3. The magnetic target separation instrument according to claim 1 or 2, wherein the connecting rod has a diameter between 0.5 mm and 5 mm.

4. The magnetic target separation instrument according to claim 1 or 2, wherein when the connecting rod has a diameter greater than 1 mm, the connecting rod has a hollow structure; and wherein a metal wire, a cable, a cord, a catheter, an optical fiber, or any combination thereof pass through the hollow structure.

5. The magnetic target separation instrument according to claim 1,
   wherein the magnetic component is a permanent magnet or soft magnet made of a magnetic material,
   wherein the magnetic material includes an alloy magnetic material, a ferrite magnetic material and an intermetallic compound magnetic material,
   wherein the magnetic material is selected from the group consisting of aluminium-nickel-cobalt, iron-chromium-cobalt, iron-cobalt-vanadium, barium ferrite, strontium ferrite, neodymium-iron-boron, samarium-cobalt, and manganese-bismuth.

6. The magnetic target separation instrument according to claim 5,
wherein the magnetic component is made of an electromagnet;
wherein the electromagnet is made of a cable-wound coil;
wherein a magnetically permeable material as an inner core is added to the cable-wound coil, and
wherein the magnetically permeable material preferably includes, comprises pure iron, ferrite soft magnetic material, iron-nickel alloy, ferrosilicon alloy, vanadium-iron-vanadium alloy, nano-crystalline soft magnetic materials, or amorphous soft magnetic materials.

7. The magnetic target separation instrument according to claim 5,
wherein the magnetic component comprises a permanent magnet, a soft magnet and an electromagnet and
wherein the high-efficiency magnetically permeable end comprises pure iron, low carbon steel, ferrosilicon alloy, ferroaluminum alloy, sendust, ferronickel alloy, iron-cobalt alloy, soft magnetic ferrite, amorphous soft magnetic alloy, or an ultra-crystalline soft magnetic alloy.

8. The magnetic target separation instrument according to claim 1,
wherein the handle is provided with
a DC power source, a power switch, and a DC battery chamber, or
an AC power source, a power switch, and an AC plug for supplying electric power for an electromagnet; or
wherein the connecting rod is made of a polymer material; or
wherein a rear end of the connecting rod comprises a permanent magnet; or
wherein a distal end of the connecting rod comprises a flexible magnetically permeable material; or
wherein the handle is provided with a regulating switch for adjusting a current magnitude.

9. The magnetic target separation instrument according to claim 1,
wherein the magnetic end is a columnar magnetic end, or a reticulated magnetic end, and
wherein the columnar magnetic end has a cross-sectional shape selected from the group consisting of a round shape, an oval shape, a polygon shape, a radial shape, a cross shape, an I-shape, a petal shape, an annular shape, a U-shape, a spiral shape, a torsion shape, a coiled shape, and a twisted shape; or
wherein the reticulated magnetic end is woven from a single- or multi-stranded magnetic or magnetically permeable materials, and
wherein the reticulated magnetic end has a shape selected from the group consisting of a woven reticulum shape, a coiled reticulum shape, a knotted rope reticulum shape, a hollow mesh, a radial reticulum shape, a convergent reticulum shape, a cross-section asymmetric reticulum shape, an open reticulum shape, a pocket-type reticulum shape, a spiral-type reticulum shape, a barrel-shaped reticulum shape, a spindle-shaped reticulum shape, an umbrella-shaped reticulum shape, a drop-shaped reticulum shape, a funnel-shaped reticulum shape, a broom-shaped reticulum shape, a disorderly entangled reticulum shape, an axial-side convergent reticulum shape, and an axial-side divergent reticulum shape; or wherein
surface of the magnetic end is coated with a biocompatible material, polytetrafluoroethylene, parylene, polyurethane, and thermoplastic polyurethane, or
surface of the magnetic end is coated with a magnetic material or a material having a magnetic permeability of $\mu>1$.

10. The magnetic target separation instrument according to claim 1, wherein there are one or two or more pieces of the steel wire or cord.

11. The magnetic target separation instrument according to claim 1,
wherein the magnetic end is integrated with an image acquisition module;
wherein the image acquisition module
comprises a lens and a CCD, or
comprises a lens and a CMOS, or
comprises a lens and an image transmission fiber, or
comprises only an image transmission fiber;
wherein the image acquisition module is composed of a lens and a CMOS;
wherein the magnetic end with the image acquisition module comprises a component for driving the magnetic end to bend;
wherein the component is fixed within the magnetic end at one end of the component, passes through the lumen of the connecting rod, and is fixed on the angle adjustment shaft of the handle at the other end of the component;
wherein there are one or two or more pieces of the component;
wherein the handle is provided with an interface for transmission of video image signal; or
wherein the component is a steel wire or cord.

12. The magnetic target separation instrument according to claim 1,
wherein the magnetic end is connected to the connecting rod in such a manner that
the magnetic end is sheathed on the distal end of the connecting rod, or
the connecting rod passes through the magnetic end, or
the connecting rod and the magnetic end are connected by bonding, or
the connecting rod and the magnetic end are connected by covering with a same material, or
the connecting rod and the magnetic end are connected by metal crimping, or
the connecting rod and the magnetic end are connected by a quick connecting mechanism; and
wherein the quick connecting mechanism includes, a screw thread, a Luer taper, a snap joint, a screw buckle, a socket component, a plug-in component, a magnetic component, or an interference fit component.

13. A method of using the magnetic target separation instrument according to claim 1, comprising:
(1) crushing stones in a body via a lithotripsy;
(2) injecting a functional material with magnetic properties into the region containing the crushed stones;
(3) magnetizing the crushed stones with the functional materials with magnetic properties; and
(4) introducing the magnetic target separation instrument to remove the crushed stones.

14. The method according to claim 13, wherein the functional materials with magnetic properties are the nanoparticles.

* * * * *